US011987803B2

(12) United States Patent
Wu et al.

(10) Patent No.: US 11,987,803 B2
(45) Date of Patent: *May 21, 2024

(54) EFFICIENT DELIVERY OF LARGE CARGOS INTO CELLS ON A POROUS SUBSTRATE

(71) Applicant: The Regents of the University of California, Oakland, CA (US)

(72) Inventors: Ting-Hsiang S. Wu, Culver City, CA (US); Pei-Yu E. Chiou, Los Angeles, CA (US); Michael A. Teitell, Tarzana, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 639 days.

This patent is subject to a terminal disclaimer.

(21) Appl. No.: 16/601,513

(22) Filed: Oct. 14, 2019

(65) Prior Publication Data

US 2020/0199628 A1 Jun. 25, 2020

Related U.S. Application Data

(63) Continuation of application No. 15/129,387, filed as application No. PCT/US2015/022813 on Mar. 26, 2015, now Pat. No. 10,472,651.

(60) Provisional application No. 61/972,145, filed on Mar. 28, 2014.

(51) Int. Cl.
| | |
|---|---|
| *C12N 15/89* | (2006.01) |
| *C12M 1/12* | (2006.01) |
| *C12M 1/26* | (2006.01) |
| *C12M 1/42* | (2006.01) |
| *C12N 15/87* | (2006.01) |

(52) U.S. Cl.
CPC ............. *C12N 15/89* (2013.01); *C12M 25/02* (2013.01); *C12M 33/04* (2013.01); *C12M 35/00* (2013.01); *C12M 35/04* (2013.01); *C12N 15/87* (2013.01)

(58) Field of Classification Search
None
See application file for complete search history.

(56) References Cited

U.S. PATENT DOCUMENTS

| | | | |
|---|---|---|---|
| 4,917,462 A | 4/1990 | Lewis et al. | |
| 5,080,586 A | 1/1992 | Kawai | |
| 5,310,674 A | 5/1994 | Weinreb et al. | |
| 6,052,286 A | 4/2000 | Worthen et al. | |
| 6,468,657 B1 | 10/2002 | Hou et al. | |
| 6,518,543 B1 | 2/2003 | Benz et al. | |
| 6,866,885 B1 | 3/2005 | Clough | |
| 7,897,377 B2 | 3/2011 | Stoppini | |
| 10,435,661 B2 | 10/2019 | Chiou et al. | |
| 10,472,651 B2 | 11/2019 | Wu et al. | |
| 10,982,217 B2 | 4/2021 | Wu et al. | |
| 2002/0023903 A1 | 2/2002 | Ann Ngoi et al. | |
| 2002/0099356 A1 | 7/2002 | Unger et al. | |
| 2003/0166181 A1 | 9/2003 | Rubinsky et al. | |
| 2003/0180946 A1 | 9/2003 | Karube et al. | |
| 2003/0235385 A1 | 12/2003 | Taylor et al. | |
| 2004/0079195 A1 | 4/2004 | Perry et al. | |
| 2004/0084304 A1 | 5/2004 | Thompson | |
| 2004/0084370 A1 | 5/2004 | Singh et al. | |
| 2004/0101822 A1 | 5/2004 | Wiesner et al. | |
| 2004/0158137 A1 | 8/2004 | Eppstein et al. | |
| 2006/0047254 A1 | 3/2006 | Akahoshi et al. | |
| 2006/0062902 A1 | 3/2006 | Sager et al. | |
| 2006/0110817 A1 | 5/2006 | Nishiyama et al. | |
| 2006/0115971 A1 | 6/2006 | Bau et al. | |
| 2006/0251874 A1 | 11/2006 | McClure et al. | |
| 2007/0173470 A1 | 7/2007 | Lin et al. | |
| 2008/0268540 A1 | 10/2008 | Ito et al. | |
| 2010/0040549 A1 | 2/2010 | Halas et al. | |
| 2010/0303722 A1 | 12/2010 | Jin et al. | |
| 2011/0117648 A1 | 5/2011 | Chiou et al. | |
| 2012/0160095 A1 | 6/2012 | Gin et al. | |
| 2012/0245042 A1 | 9/2012 | Liu et al. | |
| 2015/0044751 A1 | 2/2015 | Chiou et al. | |
| 2015/0197720 A1 | 7/2015 | Chiou et al. | |
| 2016/0017340 A1 | 1/2016 | Wu et al. | |

(Continued)

FOREIGN PATENT DOCUMENTS

| | | |
|---|---|---|
| EP | 1 448 771 B1 | 1/2007 |
| JP | H01-141582 A | 6/1989 |

(Continued)

OTHER PUBLICATIONS

U.S. Requirement for Restriction/Election dated Jun. 2, 2014 issued in U.S. Appl. No. 12/667,594.
U.S. Office Action dated Nov. 24, 2014 issued in U.S. Appl. No. 12/667,594.
U.S. Final Office Action dated Jun. 9, 2015 issued in U.S. Appl. No. 12/667,594.
U.S. Office Action dated Jul. 20, 2016 issued in U.S. Appl. No. 12/667,594.
U.S. Final Office Action dated Mar. 17, 2017 issued in U.S. Appl. No. 12/667,594.
U.S. Office Action dated May 15, 2018 issued in U.S. Appl. No. 12/667,594.

(Continued)

*Primary Examiner* — Robert M Kelly
(74) *Attorney, Agent, or Firm* — VISTA IP LAW GROUP LLP

(57) ABSTRACT

In various embodiments, method and devices for delivering large cargos (e.g., organelles, chromosomes, bacteria, and the like) into cells are provided. In certain embodiments method of delivering a large cargo into eukaryotic cells, are provided that involve providing eukaryotic cells disposed on one side of a porous membrane; providing the cargo to be delivered in a solution disposed in a reservoir chamber on the opposite side of the porous membrane; and applying pressure to the reservoir chamber sufficient to pass the cargo through pores comprising said porous membrane wherein said cargo passes through cell membranes and into the cells.

19 Claims, 7 Drawing Sheets

Specification includes a Sequence Listing.

(56) References Cited

U.S. PATENT DOCUMENTS

| | | | |
|---|---|---|---|
| 2017/0175139 | A1 | 6/2017 | Wu et al. |
| 2019/0209408 | A1* | 7/2019 | Fassihi .................. A61G 11/00 |
| 2021/0207150 | A1 | 7/2021 | Wu et al. |

FOREIGN PATENT DOCUMENTS

| | | | |
|---|---|---|---|
| JP | H08-290377 | A | 11/1996 |
| JP | 2000-023657 | A | 1/2000 |
| JP | 2002-536187 | A | 10/2002 |
| JP | 2004-041023 | A | 2/2004 |
| JP | 2005-510236 | A | 4/2005 |
| JP | 2006-515758 | A | 6/2006 |
| JP | 2008-237221 | A | 10/2008 |
| JP | 2008-238184 | A | 10/2008 |
| JP | 2011-067176 | A | 4/2011 |
| KR | 20140031943 | A | 3/2014 |
| WO | WO 98/20109 | A1 | 5/1998 |
| WO | WO 99/46588 | | 9/1999 |
| WO | WO 2003/083480 | A1 | 10/2003 |
| WO | WO 2004/063350 | A2 | 7/2004 |
| WO | WO 2007/008609 | A2 | 1/2007 |
| WO | WO 2008/073851 | A2 | 6/2008 |
| WO | WO 2008/127743 | A2 | 10/2008 |
| WO | WO 2009/017695 | A1 | 2/2009 |
| WO | WO 2012/158631 | A2 | 11/2012 |
| WO | WO 2014/151888 | A1 | 9/2014 |
| WO | WO 2015/148842 | A1 | 10/2015 |

OTHER PUBLICATIONS

U.S. Requirement for Restriction/Election dated May 11, 2016 issued in U.S. Appl. No. 14/117,543.
U.S. Office Action dated Oct. 26, 2016 issued in U.S. Appl. No. 14/117,543.
U.S. Requirement for Restriction/Election dated Nov. 22, 2016 issued in U.S. Appl. No. 14/523,254.
U.S. Office Action dated May 15, 2017 issued in U.S. Appl. No. 14/523,254.
U.S. Final Office Action dated Jan. 26, 2018 issued in U.S. Appl. No. 14/523,254.
U.S. Office Action dated Aug. 16, 2018 issued in U.S. Appl. No. 14/523,254.
U.S. Notice of Allowance dated May 7, 2019 issued in U.S. Appl. No. 14/523,254.
U.S. Requirement for Restriction/Election dated Dec. 30, 2016 issued in U.S. Appl. No. 14/771,478.
U.S. Office Action dated Mar. 22, 2017 issued in U.S. Appl. No. 14/771,478.
U.S. Final Office Action dated Dec. 26, 2017 issued in U.S. Appl. No. 14/771,478.
U.S. Office Action dated Sep. 28, 2018 issued in U.S. Appl. No. 14/771,478.
U.S. Final Office Action dated Jun. 7, 2019 issued in U.S. Appl. No. 14/771,478.
U.S. Office Action dated Jan. 30, 2018 issued in U.S. Appl. No. 15/129,387.
U.S. Final Office Action dated Oct. 17, 2018 issued in U.S. Appl. No. 15/129,387.
U.S. Office Action dated Mar. 22, 2019 issued in U.S. Appl. No. 15/129,387.
U.S. Notice of Allowance dated Jul. 31, 2019 issued in U.S. Appl. No. 15/129,387.
PCT International Search Report and Written Opinion dated Dec. 22, 2008 issued in PCT/US2008/009090.
PCT International Preliminary Report on Patentability dated Jan. 26, 2010 issued in PCT/US2008/009090.
PCT International Search Report and Written Opinion dated Nov. 1, 2012 issued in PCT/US2012/037810.
PCT International Preliminary Report on Patentability dated Nov. 19, 2013 issued in PCT/US2012/037810.

Australian Patent Examination Report No. 1 dated Jun. 26, 2016 issued in AU 2012255988.
Australian Patent Examination Report No. 2 dated Jun. 13, 2017 issued in AU 2012255988.
Canadian Office Action dated Mar. 12, 2018 issued in CA 2,873,204.
Canadian Office Action dated Mar. 14, 2019 issued in CA 2,873,204.
Canadian 3rd Office Action dated Apr. 20, 2020 issued in CA 2,873,204.
Chinese Office Action dated Sep. 10, 2014 issued in CN 201280034358.5.
Chinese Office Action [description in English] dated Nov. 30, 2016 issued in CN 201510509151.4.
Chinese Second Office Action [No Translation Available] dated Oct. 17, 2017 issued in CN 201510509151.4.
European Extended Search Report dated Nov. 10, 2014 issued in EP 12 785 188.9.
European Office Action dated Jun. 14, 2016 issued in EP 12 785 188.9.
European reply to the Communication from the Examining Division of Jun. 14, 2016, dated Dec. 23, 2016 for EP 12 785 188.9.
European Office Action dated Jul. 12, 2017 issued in EP 12 785 188.9.
European Office Action dated Feb. 13, 2018 issued in EP 12 785 188.9.
Japanese Office Action (Notice of Reasons for Rejection) dated Jan. 18, 2016 issued in JP 2014-510543.
Japanese Second Office Action (Notice of Reasons for Rejection) dated Sep. 16, 2016 issued in JP 2014-510543.
Japanese Office Action (Notice of Reasons for Rejection) dated Jun. 4, 2018 issued in JP 2017-093726.
Japanese Office Action (Notice of Reasons for Rejection) dated Apr. 8, 2019 issued in JP 2017-093726.
Korean Office Action dated Apr. 18, 2018 issued in KR 10-2013-7033131 .
PCT International Search Report and Written Opinion dated Jul. 25, 2014 issued in PCT/US2014/026618.
PCT Corrected Written Opinion dated Jul. 29, 2014 issued in PCT/US2014/026618.
PCT International Preliminary Report on Patentability dated Sep. 24, 2015 issued in PCT/US2014/026618.
Australian Examination report No. 1 dated May 25, 2019 issued in AU 2014236747.
Canadian Office Action dated Jan. 21, 2020 issued in CA 2,905,999.
Chinese Office Action dated Apr. 25, 2018 issued in CN 201480015382.3.
Chinese Second Office Action dated May 27, 2019 issued in CN 201480015382.3.
European Extended Search Report dated Sep. 23, 2016 issued in EP 14 76 8087.0.
European Office Action dated Sep. 4, 2017 issued in EP 14 76 8087.0.
European Second Office Action dated May 22, 2018 issued in EP 14 76 8087.0
European Third Office Action dated Mar. 13, 2019 issued in EP 14 76 8087.0.
European Fourth Office Action dated Sep. 4, 2019 issued in EP 14 76 8087.0.
European Fifth Office Action dated Apr. 3, 2020 issued in EP 14768087.0.
Israeli Office Action dated Oct. 25, 2018 issued in IL 241150.
Israeli 2nd Office Action dated Nov. 13, 2019 issued in IL 241150.
Japanese Office Action dated Mar. 5, 2018 issued in JP 2016-502195.
Japanese Office Action dated Feb. 18, 2019 issued in JP 2016-502195.
Korean Office Action dated Feb. 10, 2020 issued in KR 10-2015-7027342.
PCT International Search Report and Written Opinion dated Jun. 25, 2015 issued in PCT/US2015/022813.
PCT International Preliminary Report on Patentability dated Oct. 13, 2016 issued in PCT/US2015/022813.
Chinese Office Action dated Feb. 3, 2019 issued in CN 201580026218.7.

(56) References Cited

OTHER PUBLICATIONS

Chinese 2nd Office Action dated Sep. 11, 2019 issued in CN 201580026218.7.
Chinese Decision of Rejection dated Dec. 3, 2019 issued in CN 201580026218.7.
European Partial Supplementary Search Report dated Nov. 7, 2017 issued in EP 15769138.7.
European Extended Search Report dated Feb. 9, 2018 issued in EP 15769138.7.
Israeli Office Action dated Jul. 17, 2019 issued in IL 248092.
Japanese Office Action dated Feb. 4, 2019 issued in JP 2017-502931.
Japanese Final Rejection dated Sep. 17, 2019 issued in JP 2017-502931.
Japanese Pre-Appeal Report dated Apr. 1, 2020 issued in JP 2017-502931.
Adar (2017) "Raman Polarization Measurements: Keeping Track of the Instrumental Components" *Spectroscopy*, 32(2): 14-22.
Boudes et al. (2008) "Single-cell electroporation of adult sensory neurons for gene screening with RNA interference mechanism," *J. Neurosci. Methods*, 170:204-211.
Bruening and Adusumilli, (2011) "Polyelectrolyte Multilayer Films and Membrane Functionalization," *Material Matters*, 6(3): 1-6.
Cao et al. (2007) "Plasmon-Assisted Local Temperature Control to Pattern Individual Semiconductor Nanowires and Carbon Nanotubes" *Nano Lett.* 7(11):3523-3527.
Chu et al. (1987) "Electroporation for the efficient transfection of mammalian cells with DNA," *Nucleic Acids Res.*, 15(3):1311-1326.
Clark et al. (2006) "Optoinjection for efficient targeted delivery of a broad range of compounds and macromolecules into diverse cell types," *J. Biomed. Opt.*, 11(1):014034(1-8).
Enders et al. (2006) "Reversible adsorption of Au nanoparticles on $SiO_2$/Si: An in situ ATR-IR study," *Surface Science*, 600(6): L71-L75, [retrieved on Nov. 7, 2008 from the Internet: http://www.sciencedirect.com/science?_ob=ArticleURL&_udi=B6TVX-4J5T4WS-7&_user=10&_rdoc=1&_fmt=&_orig=search&_sort=d&view=c&_acct-C000050221&_version=1&_urlVersion=0&_userid=10&md5=2e06d566ab4cc63face36f61c56446b5] Abstract only, 2pp.
Han et al. (2008) "High-efficiency DNA injection into a single human mesenchymal stem cell using a nanoneedle and atomic force microscopy," *J. Nanomed. Nanotechnol. Biol. Med.*, 4(3):215-225.
Heinemann et al, (Mar. 2013) "Gold Nanoparticle Mediated Laser Transfection for Efficient siRNA Mediated Gene Knock Down," PLOS One, 8(3):e58604, pp. 1-9.
Hellman et al. (2008) "Biophysical Response to Pulsed Laser Microbeam-Induced Cell Lysis and Molecular Delivery," *J. Biophoton.*, 1(1):24-35.
Hirst et al. (2005) "Microchannel Systems in Titanium and Silicon for Structural and Mechanical Studies of Aligned Protein Self-Assemblies," *Langmuir*, 21(9):3910-3914.
Hurtig et al. (2008) "Injection and transport of bacteria in nanotube-vesicle networks," *Soft Matter*,4:1515-1520.
Jain et al. (2007) "Au nanoparticles target cancer," *Nano Today*, 2(1):18-29.
Kitamura et al.(2008) "Targeted patch-clamp recordings and single-cell electroporation of unlabeled neurons in vivo," *Nat. Methods*, 5(1):61-67.
Kotaidis et al. (2006) "Excitation of nanoscale vapor bubbles at the surface of gold nanoparticles in water," *The Journal of Chemical Physics*, 124:184702(1-7).
Laffafian et al. (1998) "Lipid-assisted microinjection: introducing material into the cytosol and membranes of small cells," *Biophys. J.*, 75:2558-2563.
Lapotko et al. (2006) "Selective laser nano-thermolysis of human leukemia cells with microbubbles generated around clusters of gold nanoparticles," *Laser Surg. Med.*, 38:631-642.
Lee et al. (2009) "Remote Optical Switch for Localized and Selective Control of Gene Interference," *Nano Lett.*, 9(2):562-570.
Lin et al. (Jun. 21-25, 2015) "Shape Anisotropic Magnetic Particles For High Throughput And High Efficiecy Intracelluar Delivery Of Functional Macromolecules," *IEEE, Transducers 2015, 18th International Conference on Solid-State Sensors, Actuators and Microsystems (Transducers)*, Anchorage, Alaska, USA, pp. 880-883.
Link et al (1999) "Spectral Properties and Relaxation Dynamics of Surface Plasmon Electronic Oscillations in Gold and Silver Nanodots and Nanorods," *J. Phys. Chem. B*, 103(40):8410-8426.
Liu et al. (2005) "Optofluidic control using photothermal nanoparticles," *Nat. Mater.*, 5:27-32.
Lokhandwalla et al. (2001) "Mechanical haemolysis in shock wave lithotripsy (SWL): I. Analysis of cell deformation due to SWL flow-fields," *Phys. Med. Biol.*, 46:413-437.
Lukianova-Hleb et al. (2010) "Plasmonic Nanobubbles as Transient Vapor Nanobubbles Generated around Plasmonic Nanoparticles," *ACS Nano*, 4(4):2109-2123.
Madeira, et al. (2010) "Nonviral Gene Delivery to Mesenchymal Stem Cells Using Cationic Liposomes for Gene and Cell Therapy," *Journal of Biomedicine and Biotechnology*, vol. 2010, Article ID 73539, pp. 1-12.
Marmottant et al. (2003) "Controlled vesicle deformation and lysis by single oscillating bubbles," *Nature*, 423:153-156.
Menon and Martin (1995) "Fabrication and Evaluation of Nanoelectrode Ensembles," *Anal. Chem.*, 67(13): 1920-1928.
Mitragotri (2005) "Innovation—Healing sound: the use of ultrasound in drug delivery and other therapeutic applications," *Nat. Rev. Drug Discovery*, 4(3):255-260.
Parker et al. (Jul. 13, 2010) "Bulk Titanium Microfluidic Networks For Protein Self-Assembly Studies," [Retrieved on Oct. 23, 14 from the Internet at URL:http://www.engineering.ucsb.edu/memsucsb/Research/publications/parker_microtas05.pdf], 4 pp.
Pitsillides et al. (2003) "Selective cell targeting with light-absorbing microparticles and nanoparticles," *Biophys. J.*, 84(6):4023-4032.
Prodan et al. (2003) "A Hybridization Model for the Plasmon Response of Complex Nanostructures," *Science*, 302:419-422.
Qiu et al. (2009) "Microchip CE analysis of amino acids on a titanium dioxide nanoparticles-coated PDMS microfluidic device with in-channel indirect amperometric detection," *Electrophoresis*, 30(19):3472-3479.
Shvedov et al. (2009) "Optical guiding of absorbing nanoclusters in air," *Optics Express*, 17(7):5743-5757.
Shi et al. (2004) "Myogenic fusion of hurnan bone marrow stromal cells, but not hematopoietic cells", *Blood* 104(1): 290-294.
Shi et al. (2010) "Pressure Regulated Biomolecule Injection Into Nih 3t3 Cells Through Integrated Nano/Mesopores", *14th International Conference on Miniaturized Systems for Chemistry and Life Sciences* Oct. 3-7, 2010, Groningen, The Netherlands, pp. 491-493, Retrieved from the Internet: URL:http://www.rsc.orgjbinariesjlocj2010/pdfs/Papers/171 0548.pdf [retrieved on Oct. 24, 2017].
Skirtach et al. (2005) "The Role of Metal Nanoparticles in Remote Release of Encapsulated Materials," *Nano Lett.*, 5(7):1371-1377.
Stevenson et al. (2006) "Femtosecond optical transfection of cells:viability and efficiency," *Opt. Express*, 14(16):7125-7133.
Suzuki et al. (2010) "A Cell Array Fabricated by Assembly-Free Multidirectional Photolithography," *Journal of Japan Institute of Electronics Packaging*, 13(3):194-199.
Tirlapur et al. (2002) "Cell biology: Targeted transfection by femtosecond laser," Nature, 418:290-291.
Vogel et al. (2005) "Mechanisms of femtosecond laser nanosurgery of cells and tissues," *Appl. Phys. B: Laser Opt.*, 81(8):1015-1047.
Waje et al. (2005) "Deposition of platinum nanoparticles on organic functionalized carbon nanotubes grown in situ on carbon paper for fuel cells," *Nanotechnology*, 16:S395-S400.
Wu et al. (Jul. 21, 2008) "Light Image Patterned Molecular Delivery into Live Cells Using Gold Particle Coated Substrate," *IEEE/LEOS Summer Topical Meetings, 2008 Digest of the IEEE*, Piscataway, NJ, USA, pp. 195-196.
Wu et al. (Feb. 7, 2010) "Molecular Delivery Into Live Cells Using Gold Nanoparticle Arrays Fabricated By Polymer Mold Guided Near-Field Photothermal Annealing," *Proceedings of ASME 2010 First Global Congress on NanoEngineering for Medicine and Biology*, Houston Texas, USA, pp. 121-122.
Wu et al. (2010) "Image patterned molecular delivery into live cells using gold particle coated substrates," *Opt. Express*, 18(2):938-946.

(56) References Cited

OTHER PUBLICATIONS

Wu et al. (2010) "Photothermal nanoblade for patterned cell membrane cutting," *Optics Express*, 18(22):23153-23160.
Wu et al. (2011) "Photothermal nanoblade for Large Cargo Delivery into Mammalian Cells," *Anal. Chem.*, 83(4):1321-1327.
Wu et al. (May 1, 2015) "Massively parallel delivery of large cargo into mammalian cells with light pulses," *Nature Methods* [*HHS Public Access Author Manuscript*], 12(5):439-444 and Supplementary information (Apr. 6, 2015) 2pp.
Xia et al. (2011) "Gold Nanocages: From Synthesis to Theranostic Applications," *Acc. Chem. Res*, 44(10): 914-924.
Yu et al. (2012) "Gold Coated Block Copolymer Membranes with Precisely Controllable Pore Size for Molecule Separations," *Procedia Engineering*, 44: 1639-1641.
Yue et al. (2010) "Study of transportation of atrazine and paraquat through nanochannels," *Journal of Membrane Science*, 3556:117-122.
Zhang, Y. (2007) "Microinjection technique and protocol to single cells," *Nat. Protoc.* published online Nov. 2, 2007 [retrieved on May 13, 2011 at 3:04 PM from the Internet at http://www.natureprotocols.com/2007/11/02/microinjection_technique_and_p.php], pp. 1-11.
Zhao et al. (2009) "Wafer level bulk titanium ICP etching using SU8 as an etching mask," *J. Micromech. Microeng.*, 19(9):95006, 10pp.
Australian Examination report No. 1 dated Jul. 30, 2020 issued in AU 2015235932.
Australian Examination report No. 2 dated Jul. 9, 2021 issued in AU 2015235932.
Buruiana et al. (2018) "Transparent Dielectric Materials," Taylor & Francis Group—Chapter 5, 96-123 (30 pages).
Canadian Office Action dated Feb. 11, 2021 issued in CA 2,947,539.
Chinese Rejection Decision dated Sep. 1, 2020 issued in CN 201480015382.3.
Chinese Third Office Action dated Jun. 4, 2020 issued in CN 201480015382.3.
EP Office Action dated May 31, 2022, in Application No. EP15769138.7.
Japanese Office Action dated Feb. 8, 2021 issued in JP 2020-005893.
JP Office Action dated Dec. 13, 2021, in Application No. 2020005893 with English Translation.
Korean Office Action dated Mar. 26, 2021 issued in KR 10-2016-7029900.
Uchugonova et al. (2008) "Targeted transfection of stem cells with sub-20 femtosecond laser pulses" Optics Express 13: 9357-9364.
U.S. Final Office Action dated Jul. 10, 2020 issued in U.S. Appl. No. 14/771,478.
U.S. Notice of Allowance dated Dec. 9, 2020 issued in U.S. Appl. No. 14/771,478.

* cited by examiner (i)

(ii)

(iii)

Transformed cells with
delivered mitochondria

SEQUENCE LISTING

```
<160> NUMBER OF SEQ ID NOS: 3

<210> SEQ ID NO 1
<211> LENGTH: 200
<212> TYPE: DNA
<213> ORGANISM: Homo sapiens

<400> SEQUENCE: 1
cattactgcc agccaccatg aatattgcac ggtaccataa atacttgacc acctgtagta     60
cataaaaacc caatccacat caaaaccccc accccatgct tacaagcaag tacagcaatc    120
aaccttcaac tatcacacat caactgcaac tccaaagcca cccctcaccc actaggatat    180
caacaaacct acccaccctt                                                200

<210> SEQ ID NO 2
<211> LENGTH: 200
<212> TYPE: DNA
<213> ORGANISM: Homo sapiens

<400> SEQUENCE: 2
cattactgcc agccaccatg aatattgtac agtaccataa atacttgacc acctgtagta     60
cataaaaacc caatccacat caaaaccccc tccccatgct tacaagcaag tacagcaatc    120
aaccctcaac tatcacacat caactgcaac tccaaagcca cccctcaccc actaggatac    180
caacaaacct acccaccctt                                                200

<210> SEQ ID NO 3
<211> LENGTH: 200
<212> TYPE: DNA
<213> ORGANISM: Homo sapiens
<220> FEATURE:
<221> NAME/KEY: misc_feature
<222> LOCATION: (65)..(65)
<223> OTHER INFORMATION: n is a, c, g, or t
```

```
<400> SEQUENCE: 3
cattactgcc agccaccatg aatattgtac agtaccataa atacttgacc acctgtagta        60
catanaaacc caatccacat caaaacccccc tccccatgct tacaagcaag tacagcaatc      120
aaccctcaac tatcacacat caactgcaac tccaaagcca ccccctcaccc actaggatac      180 caacaaacct acccacccttt                                                   200
```

EFFICIENT DELIVERY OF LARGE CARGOS INTO CELLS ON A POROUS SUBSTRATE

CROSS-REFERENCE TO RELATED APPLICATIONS

This application is a continuation of U.S. Ser. No. 15/129,387 (U.S. Pat. No. 10,472,651), filed on Sep. 26, 2016 which is a U.S. 371 National Phase of PCT/US2015/022813, filed on Mar. 26, 2015, which claims benefit of and priority to U.S. Ser. No. 61/972,145, filed Mar. 28, 2014, all of which are incorporated herein by reference in their entirety for all purposes.

SEQUENCE LISTING

This application contains references to nucleic acid sequences which have been submitted concurrently herewith as the sequence listing text file "UCLA-P124C1US_ST25.txt", file size 1.63 kb, created on Mar. 10, 2020, which is incorporated by reference in its entirety pursuant to 37 C.F.R. 1.52(e)(5).

STATEMENT OF GOVERNMENTAL SUPPORT

[Not Applicable]

BACKGROUND

Transferring cargo into mammalian cells over a wide range of 1 sizes, including proteins, DNA, RNA, chromosomes, nuclei, and inanimate particles, such as quantum dots, surface-enhanced Raman scattering (SERS) particles, and microbeads, is highly desirable in many fields of biology. Delivery methods, such as endocytosis, can entrap cargo in an endosome, where the low pH microenvironment and lytic enzymes often lead to cargo degradation (Luo and Saltzman (2000) *Nat. Biotechnol.* 18: 33-37). Viral and chemical delivery methods package the cargo inside a virus or form chemical complexes that enhance uptake (Naldini et al. (1996) *Science*, 272: 263-267; Feigner et al. (1987) *Proc. Natl. Acad Sci. USA*, 84: 7413-7417). However, toxicity, cell-type specific uptake, and more importantly limited cargo packing capacity impose a significant constraint on cargo size and transferable cell types (Luo and Saltzman, supra.).

Physical transfer methods include electroporation (Chu, et al. (1987) *Nucleic Acids Res.* 15: 1311-1326) and sonoporation (Mitragotri (2005) *Nat. Rev. Drug Discovery*, 4: 255-260), which produce randomly distributed nanoscale pores, and optoporation (Tirlapur and Konig (2002) *Nature*, 418: 290-291; Vogel, et al. (2005) *Appl. Phys. B: Laser Opt.*, 81: 1015-1047; Clark et al. (2006) *J. Biomed. Opt.*, 11: 014034), which generates pores on the cell membrane at the laser focal point. Through these pores, small cargo is delivered into cells by thermal diffusion or by an electric field. Delivery of large cargo with these methods has low efficiency due to the slow speed of cargo diffusion and decreasing cell viability with increasing pore size (Stevenson et al. (2006) *Opt. Express*, 14: 7125-7133). Microcapillary injection (King (2004) *Methods in Molecular Biology* 245: *Gene Delivery to Mammalian Cells* 1; Humana Press Inc.: Totowa, NJ) uses a sharp lass tip to mechanically penetrate a cell membrane for delivery. However, mechanical trauma from membrane penetration limits the typical pipet tip to 0.5 um in diameter in order to maintain cell viability (Han et al. (2998) *J. Nanomed Nanotechnol. Biol. Med.*, 4: 215-225). Cargo larger than the pipet tip cannot be injected due to pipet clogging and cargo shearing. Electro-injection, which combines electroporation with microcapillary injection, has demonstrated small molecule delivery, such as RNA and plasmid DNA, into live cells (Boudes et al. (208) *J. Neurosci. Meth.*, 170: 204-211; Kitamura et al. (2008) *Nat. Meth.*, 5: 61-67) and bacteria delivery into artificial lipid vesicles (Hurtig and Orwar (2008) *Soft Matter*, 4: 1515-1520) by weakening the contacting cell membrane with an electric field, followed by gentle mechanical penetration into the cell. Alternatively, a simple lipid assisted microinjection (SLAM) technique (Laffafian and Hallett (1998) *Biophys.* 1, 75: 2558-2563) incorporates synthetic lipid molecules at the tip of a glass microcapillary. Contact of the SLAM micropipette with a cell membrane allowed the lipid molecules to fuse with the cell membrane to form a continuous and temporary pathway for cargo delivery. This method avoids the zigzag stabbing motion of the micropipette tip through the cell membrane. However, the lipophilic interactions with cargo and cell membrane can produce unwanted biological effects in the cell as well as with the delivery cargo, limiting this method to specific cell types and cargo contents.

SUMMARY

In various aspects, the invention(s) contemplated herein may include, but need not be limited to, any one or more of the following embodiments:

Embodiment 1: A method of delivering a large cargo into eukaryotic cells, said method including: providing said cells disposed on one side of a porous membrane; providing said cargo in a solution disposed in a reservoir chamber on the opposite side of said porous membrane; and applying pressure to said reservoir chamber sufficient to pass said cargo through pores including said porous membrane wherein said cargo passes through cell membrane and into said cells.

Embodiment 2: The method of embodiment 1, wherein said reservoir chamber ranges in volume from about 10 µL up to about 500 µL, or from about 40 µL to about 500 µL, or from about 50 µL to about 400 µL, or from about 60 µL to about 300 µL, or from about 704, to about 200 µL, or from about 80 µL to about 150 µL, or from about 10 µL up to about 1 mL, or from about 10 µL up to about 500 µL, or from about 10 µL up to about 100 µL.

Embodiment 3: The method of embodiment 2, wherein said reservoir chamber has a volume of about 100 µL.

Embodiment 4: The method according to any one of embodiments 1-3, wherein said porous membrane ranges in thickness from about 5 µm to about 30 µm, or from about 5 µm to about 20 µm, or from about 5 µm to about 15 µm.

Embodiment 5: The method of embodiment 4, wherein said porous membrane has a thickness of about 10 µm.

Embodiment 6: The method according to any one of embodiments 1-5, wherein the average or median pore size of said porous membrane ranges from about 100 nm up to about 20 µm or up to about 20 µm, or from about 500 nm up to about 8 µm, or from about 1 µm up to about 5 µm.

Embodiment 7: The method of embodiment 6, wherein the median or average pore size in said porous membrane is about 1 µm.

Embodiment 8: The method of embodiment 6, wherein the median or average pore size in said porous membrane is about 3 µm.

Embodiment 9: The method of embodiment 6, wherein the median or average pore size in said porous membrane is about 5 µm.

Embodiment 10: The method according to any one of embodiments 1-9, wherein said porous membrane includes about $1 \times 10^5$ pores/cm$^2$ up to about $1 \times 10^7$ pores/cm$^2$, or about $5 \times 10^5$ pores/cm$^2$ up to about $5 \times 10^6$, or about $1 \times 10^5$ pores/cm$^2$ up to about $1 \times 10^7$ pores/cm$^2$.

Embodiment 11: The method of embodiment 10, wherein said porous membrane includes about a 1 μm diameter average pore size at about $1.6 \times 10^6$ pores/cm$^2$.

Embodiment 12: The method of embodiment 10, wherein said porous membrane includes about a 3 μm diameter average pore size at about $8 \times 10^5$ pores/cm$^2$.

Embodiment 13: The method according to any one of embodiments 1-12, wherein said membrane includes a polymer membrane.

Embodiment 14: The method according to any one of embodiments 1-12, wherein said membrane includes a material selected from the group consisting of a nylon membrane, a nylon mesh, a filer membrane, a polytetrafluoroethylene (PTFE) membrane, an expanded polytetrafluoroethylene (ePTFE) membrane, a polyester membrane, a polyetheretherketone (PEEK) membrane, an expanded polyetheretherketone (ePEEK) membrane, aa polyethylene (PE) membrane, a polypropylene (PP) membrane, a polyvinylidene fluoride (PVDF) membrane, an ethyl vinyl acetate (EVA) membrane, a thermoplastic polyurethane (TPU) membrane, a polyethersulfone (PES) membrane, a polycarbonate membrane, and a polyethylene terephthalate (PET) membrane.

Embodiment 15: The method of embodiment 14, wherein said membrane includes a polyester membrane, a polycarbonate membrane, or a polyethylene terephthalate (PET) membrane.

Embodiment 16: The method according to any one of embodiments 1-15, wherein said applying pressure produces a deflection of said porous membrane.

Embodiment 17: The method of embodiment 16, wherein said deflection ranges from about 20 μm, or from about 50 μm, or from about 100 μm, or from about 500 μm up to about to about 1 cm, or up to about 500 mm, or up to about 300 mm, or up to about 100 mm.

Embodiment 18: The method according to any one of embodiments 1-17, wherein said applying pressure includes applying a transient pressure.

Embodiment 19: The method according to any one of embodiments 1-18, wherein said applying pressure includes applying pressure for about 1 msec up to about 1 minute or from about 100 msec up to about 1 minute, or from about 1 sec up to about 1 min.

Embodiment 20: The method according to any one of embodiments 1-19, wherein said applying pressure includes applying pressure through a port into said reservoir chamber.

Embodiment 21: The method according to any one of embodiments 1-19, wherein said applying pressure includes deflecting a wall of said reservoir chamber when said chamber is filled and closed.

Embodiment 22: The method according to any one of embodiments 1-19, wherein said applying pressure includes injecting a solution through a wall of said reservoir chamber.

Embodiment 23: The method according to any one of embodiments 1-22, wherein said providing said cargo in a solution disposed in a reservoir chamber includes introducing said solution through a port into said reservoir chamber.

Embodiment 24: The method according to any one of embodiments 1-22, wherein said providing said cargo in a solution disposed in a reservoir chamber includes pipetting the cargo solution into the reservoir.

Embodiment 25: The method according to any one of embodiments 1-22, wherein said providing said cargo in a solution disposed in a reservoir chamber includes loading said reservoir chamber before placing said porous membrane on or in said chamber.

Embodiment 26: The method according to any one of embodiments 1-22, wherein said providing said cargo in a solution disposed in a reservoir chamber includes injecting said solution through a needle that penetrates a wall of said reservoir chamber.

Embodiment 27: The method according to any one of embodiments 1-22, wherein said providing said cargo in a solution disposed in a reservoir chamber includes passing said solution through said membrane to load said reservoir chamber.

Embodiment 28: The method according to any one of embodiments 1-27, wherein said cargo includes one or moieties selected from the group consisting of a natural chromosome or chromosome fragment, a synthetic chromosome, a bacterium, a synthetic particle, an intracellular fungus, an intracellular protozoan, DNA and/or RNA packaged in a liposome (e.g., lipofectamine), and an organelle.

Embodiment 29: The method of embodiment 28, wherein said cargo includes a cell nucleus.

Embodiment 30: The method of embodiment 28, wherein said cargo includes a mitochondria.

Embodiment 31: The method of embodiment 28, wherein said cargo includes a chromosome or chromosome fragment.

Embodiment 32: The method of embodiment 28, wherein said cargo includes an artificial chromosome.

Embodiment 33: The method of embodiment 28, wherein said cargo includes a bacterium.

Embodiment 34: The method according to any one of embodiments 1-33, wherein said cells are selected from the group consisting of vertebrate cells, fungal cells, and yeast cells.

Embodiment 35: The method according to any one of embodiments 1-33, wherein said cells are selected from the group consisting of mammalian cells, insect cells, and invertebrate cells.

Embodiment 36: The method of embodiment 35, wherein said cells comprise mammalian cells.

Embodiment 37: The method of embodiment 35, wherein said cells comprise human cells.

Embodiment 38: The method of embodiment 35, wherein said cells comprise non-human mammalian cells.

Embodiment 39: The method according to any one of embodiments 36-38, wherein said cells comprise lymphocytes, or stem cells.

Embodiment 40: The method of embodiment 39, wherein said cells comprise stem cells selected from the group consisting of adult stem cells, embryonic stem cells, cord blood stem cells and induced pluripotent stem cells.

Embodiment 41: The method according to any one of embodiments 36-38, wherein said cells comprise differentiated somatic cells.

Embodiment 42: The method according to any one of embodiments 1-33, wherein said cells comprise cells from a cell line.

Embodiment 43: The method of embodiment 42, wherein said cells comprise cells from a cell line listed in Table 1.

Embodiment 44: The method of embodiment 42, wherein said cells comprise cells from a cell line selected from the group consisting of HeLa, National Cancer Institute's 60 cancer cell lines (NCI60), ESTDAB database, DU145 (prostate cancer), Lncap (prostate cancer), MCF-7 (breast cancer), MDA-MB-438 (breast cancer), PC3 (prostate cancer), T47D (breast cancer), THP-1 (acute myeloid leukemia), U87 (glioblastoma), SHSY5Y Human neuroblastoma cells, cloned from a myeloma, and Saos-2 cells (bone cancer).

Embodiment 45: The method according to any one of embodiments 1-44, wherein said cells are cultured on said porous membrane.

Embodiment 46: The method according to any one of embodiments 1-44, wherein said cells are cultured as an adherent layer on said porous membrane.

Embodiment 47: The method according to any one of embodiments 45-46, wherein said cells are cultured to confluence on said porous membrane.

Embodiment 48: The method according to any one of embodiments 1-47, wherein said porous membrane does not bear a metallic film or metallic nanoparticles.

Embodiment 49: The method according to any one of embodiments 1-48, wherein said method does not involve heating a surface of said membrane.

Embodiment 50: The method according to any one of embodiments 1-48, wherein said method does not involve heating a surface of said membrane with a laser.

Embodiment 51: A device for delivering a large cargo into eukaryotic cells, said device including: a porous membrane; and a reservoir chamber on one side of said porous membrane, where the volume of said reservoir chamber is less than about 500 µL.

Embodiment 52: The device of embodiment 51, wherein said reservoir chamber ranges in volume from about 40 µL to about 500 µL, or from about 50 µL to about 400 µL, or from about 60 µL to about 300 µL, or from about 70 µL to about 200 µL, or from about 80 µL to about 150 µL, or from about 10 µL up to about 100 µL.

Embodiment 53: The device of embodiment 2, wherein said reservoir chamber has a volume of about 100 µL.

Embodiment 54: The device according to any one of embodiments 51-53, wherein said porous membrane ranges in thickness from about 5 µm to about 30 µm, or from about 5 µm to about 20 µm, or from about 5 µm to about 15 µm.

Embodiment 55: The device of embodiment 54, wherein said porous membrane has a thickness of about 10 µm.

Embodiment 56: The device according to any one of embodiments 51-55, wherein the average or median pore size of said porous membrane ranges from about 100 nm up to about 20 µm or up to about 20 µm, or from about 500 nm up to about 8 µm, or from about 1 µm up to about 5 µm.

Embodiment 57: The device of embodiment 56, wherein the median or average pore size in said porous membrane is about 1 µm.

Embodiment 58: The device of embodiment 56, wherein the median or average pore size in said porous membrane is about 3 µm.

Embodiment 59: The device of embodiment 56, wherein the median or average pore size in said porous membrane is about 5 µm.

Embodiment 60: The device according to any one of embodiments 51-59, wherein said porous membrane includes about $1\times10^5$ pores/cm$^2$ up to about $1\times10^7$ pores/cm$^2$, or about $5\times10^5$ pores/cm$^2$ up to about $5\times10^6$, or about $1\times10^5$ pores/cm$^2$ up to about $1\times10^7$ pores/cm$^2$.

Embodiment 61: The device of embodiment 60, wherein said porous membrane includes about a 1 µm diameter average pore size at about $1.6\times10^6$ pores/cm$^2$.

Embodiment 62: The device of embodiment 60, wherein said porous membrane includes about a 3 µm diameter average pore size at about $8\times10^5$ pores/cm$^2$.

Embodiment 63: The device according to any one of embodiments 51-62, wherein said membrane includes a polymer membrane.

Embodiment 64: The device according to any one of embodiments 51-62, wherein said membrane includes a material selected from the group consisting of a nylon membrane, a nylon mesh, a filer membrane, a polytetrafluoroethylene (PTFE) membrane, an expanded polytetrafluoroethylene (ePTFE) membrane, polyetheretherketone (PEEK) membrane, expanded polyetheretherketone (ePEEK) membrane, polyethylene (PE) membrane, polypropylene (PP) membrane, polyvinylidene fluoride (PVDF) membrane, ethyl vinyl acetate (EVA) membrane, thermoplastic polyurethane (TPU) membrane, and a polyethersulfone (PES) membrane.

Embodiment 65: The device according to any one of embodiments 51-62, wherein said membrane includes a polyester membrane, a polycarbonate membrane, or a polyethylene terephthalate (PET) membrane.

Embodiment 66: The device according to any one of embodiments 51-65, wherein said reservoir chamber is in fluid communication with a port or channel configured to introduce a solution into said chamber.

Embodiment 67: The device according to any one of embodiments 51-65, wherein said reservoir chamber closed and/or sealed (e.g., flow from the reservoir can only occur through the porous membrane).

Embodiment 68: The device according to any one of embodiments 51-65, wherein reservoir chamber contains a solution including a cargo to be delivered into said eukaryotic cells.

Embodiment 69: The device of embodiment 68, wherein said cargo includes one or moieties selected from the group consisting of a natural chromosome or chromosome fragment, a synthetic chromosome, a bacterium, a synthetic particle, an intracellular fungus, an intracellular protozoan, DNA and/or RNA packaged in a liposome or a lipid particle, and an organelle.

Embodiment 70: The device of embodiment 69, wherein said cargo includes a cell nucleus.

Embodiment 71: The device of embodiment 69, wherein said cargo includes a mitochondria.

Embodiment 72: The device of embodiment 69, wherein said cargo includes a chromosome or chromosome fragment.

Embodiment 73: The device of embodiment 69, wherein said cargo includes an artificial chromosome.

Embodiment 74: The device of embodiment 69, wherein said cargo includes a bacterium.

Embodiment 75: The device according to any one of embodiments 51-74, wherein eukaryotic cells are disposed on the surface of said porous membrane that is opposite the side juxtaposed to said reservoir chamber.

Embodiment 76: The device of embodiment 74, wherein said cells are selected from the group consisting of mammalian cells, insect cells, and invertebrate cells.

Embodiment 77: The device of embodiment 76, wherein said cells comprise mammalian cells.

Embodiment 78: The device of embodiment 76, wherein said cells comprise human cells.

Embodiment 79: The device of embodiment 76, wherein said cells comprise non-human mammalian cells.

Embodiment 80: The device according to any one of embodiments 77-79, wherein said cells comprise lymphocytes, or stem cells.

Embodiment 81: The device of embodiment 80, wherein said cells comprise stem cells selected from the group consisting of adult stem cells, embryonic stem cells, cord blood stem cells and induced pluripotent stem cells.

Embodiment 82: The device according to any one of embodiments 77-79, wherein said cells comprise differentiated somatic cells.

Embodiment 83: The device according to any one of embodiments 51-74, wherein said cells comprise cells from a cell line.

Embodiment 84: The device of embodiment 83, wherein said cells comprise cells from a cell line listed in Table 1.

Embodiment 85: The device of embodiment 83, wherein said cells comprise cells from a cell line selected from the group consisting of HeLa, National Cancer Institute's 60 cancer cell lines (NCI60), ESTDAB database, DU145 (prostate cancer), Lncap (prostate cancer), MCF-7 (breast cancer), MDA-MB-438 (breast cancer), PC3 (prostate cancer), T47D (breast cancer), THP-1 (acute myeloid leukemia), U87 (glioblastoma), SHSY5Y Human neuroblastoma cells, cloned from a myeloma, and Saos-2 cells (bone cancer).

Embodiment 86: The device according to any one of embodiments 51-85, wherein said cells are cultured on said porous membrane.

Embodiment 87: The device according to any one of embodiments 51-85, wherein said cells are cultured as an adherent layer on said porous membrane.

Embodiment 88: The device according to any one of embodiments 86-87, wherein said cells are cultured to confluence on said porous membrane.

Embodiment 89: The device according to any one of embodiments 51-88, wherein said porous membrane does not bear a metallic film or metallic nanoparticles.

Embodiment 90: The device according to any one of embodiments 51-89, wherein said method does not involve heating a surface of said membrane.

Embodiment 91: A system for delivering large cargos into eukaryotic cells, said system including: a first device according to any one of embodiments 51-90; and a second device according to any one of embodiments 51-90; wherein said first device and said second device comprise ports and/or channels that are in fluid communication with the reservoir chambers including said first device and said second device and said ports and/or channels are in fluid communication with each other; or wherein said first device and said second device comprise ports and/or channels that are in fluid communication with the reservoir chambers including said first device and said second device and said ports and/or channels are not in fluid communication with each other.

Embodiment 92: The system of embodiment 91, wherein said first device and said second device comprise ports and/or channels that are in fluid communication with the reservoir chambers including said first device and said second device and said ports and/or channels are in fluid communication with each other.

Embodiment 93: The system of embodiment 91, wherein said first device and said second device comprise ports and/or channels that are in fluid communication with the reservoir chambers including said first device and said second device and said ports and/or channels are not in fluid communication with each other.

Embodiment 94: The system of embodiment 93, wherein cargo present in the reservoir chamber of said first device is different than cargo present in the reservoir chamber of said second device.

Embodiment 95: The system according to any one of embodiments 91-94, wherein eukaryotic cells present in said first device are the same type of eukaryotic cells in said second device.

Embodiment 96: The system according to any one of embodiments 91-94, wherein eukaryotic cells present in said first device are different than the eukaryotic cells in said second device.

Embodiment 97: The system according to any one of embodiments 91-96, wherein said system includes a third device according to any one of embodiments 51-90; and said first device and said third device comprise ports and/or channels that are in fluid communication with the reservoir chambers including said first device and said third device and said ports and/or channels are in fluid communication with each other; or wherein said first device and said third device comprise ports and/or channels that are in fluid communication with the reservoir chambers including said first device and said third device and said ports and/or channels are not in fluid communication with each other.

Definitions

The term "cargo" as used herein with respect to delivery into a cell refers to any moiety that it is desired to deliver into a cell. Illustrative cargos include, but are not limited to organelles, whole chromosomes or bacteria, large nucleic acid or protein constructs, synthetic particles, and the like.

The term "large cargo" refers to cargo ranging in size from about 100 nm, or from about 500 nm, or from about 800 nm, or from about 1 μm, or from about 3 μm, or from about 5 μm up to about 20 μm, or up to about 15 μm, or up to about 10 μm (in length and/or width and/or in diameter). In certain embodiments a large cargo ranges in size from about 100 nm (e.g., DNA and/or RNA in a lipid or liposomal complex) up to about 10 μm (e.g., chromosome, nucleus, etc.).

The terms "sealed" or "closed" when used with respect to a sealed and/or closed reservoir chamber indicates that flow out of the reservoir can only occur, or occurs predominantly, through the porous membrane.

DETAILED DESCRIPTION

In various embodiments improved methods and devices for delivering cargos, especially "large" cargos into cells are provided herein. The methods and devices described herein transfer large cargos including, but not limited to, isolated mitochondria and bacteria into mammalian cells with unprecedented throughput and ease. Simultaneous delivery into has been demonstrated $10^5$ cells is achieved within seconds and cell viability (>90%) has been observed.

Figure 1:
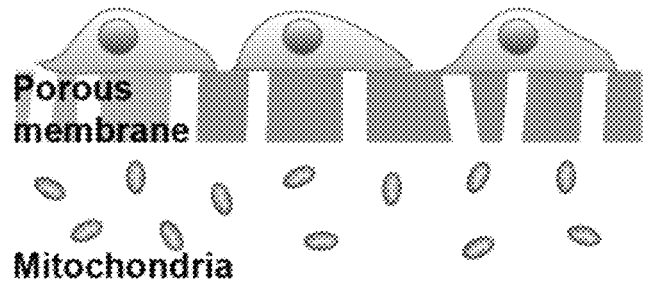
FIG. 1 show a schematic illustrating one embodiment of the delivery process.
Figure 1:
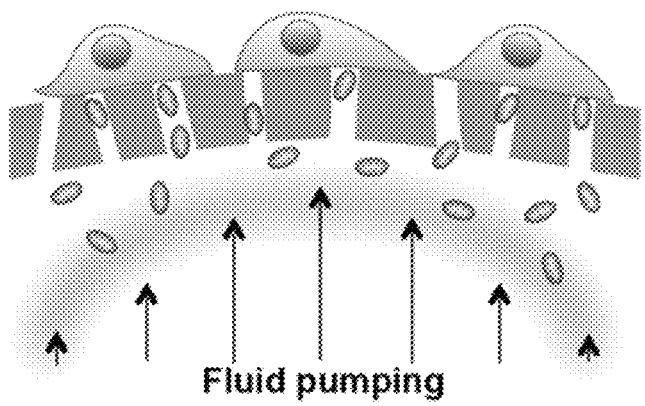
Figure 1:
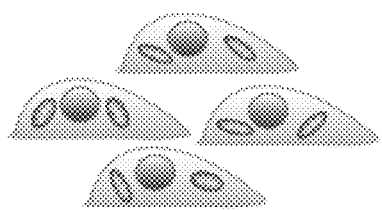

One illustrative, but non-limiting embodiment of the delivery method is depicted in FIG. 1. As shown therein, recipient cells (e.g., eukaryotic cells) are placed on or cultured on a porous membrane (e.g., a 10 µm thick polymer membrane) with through-membrane pores. The cargo that is to be transfected into the recipient cells is placed in a solution and loaded into a reservoir chamber on the opposite side of the porous membrane. Pressure is applied to the bottom reservoir chamber to pump the cargo suspension through the membrane pores towards the recipient cells. In certain embodiments the polymer membrane is deformed slightly due to the pressure driven flow. Transfected cells can be observed shortly after the pressurization.

Transfection Devices.

In certain embodiments transfection devices are provided for use in the methods described herein. In certain illustrative, but non-limiting embodiments, the transfection device comprises a porous membrane as described herein, disposed over a reservoir chamber (see, e.g., FIG. 2A).

Figure 2A:
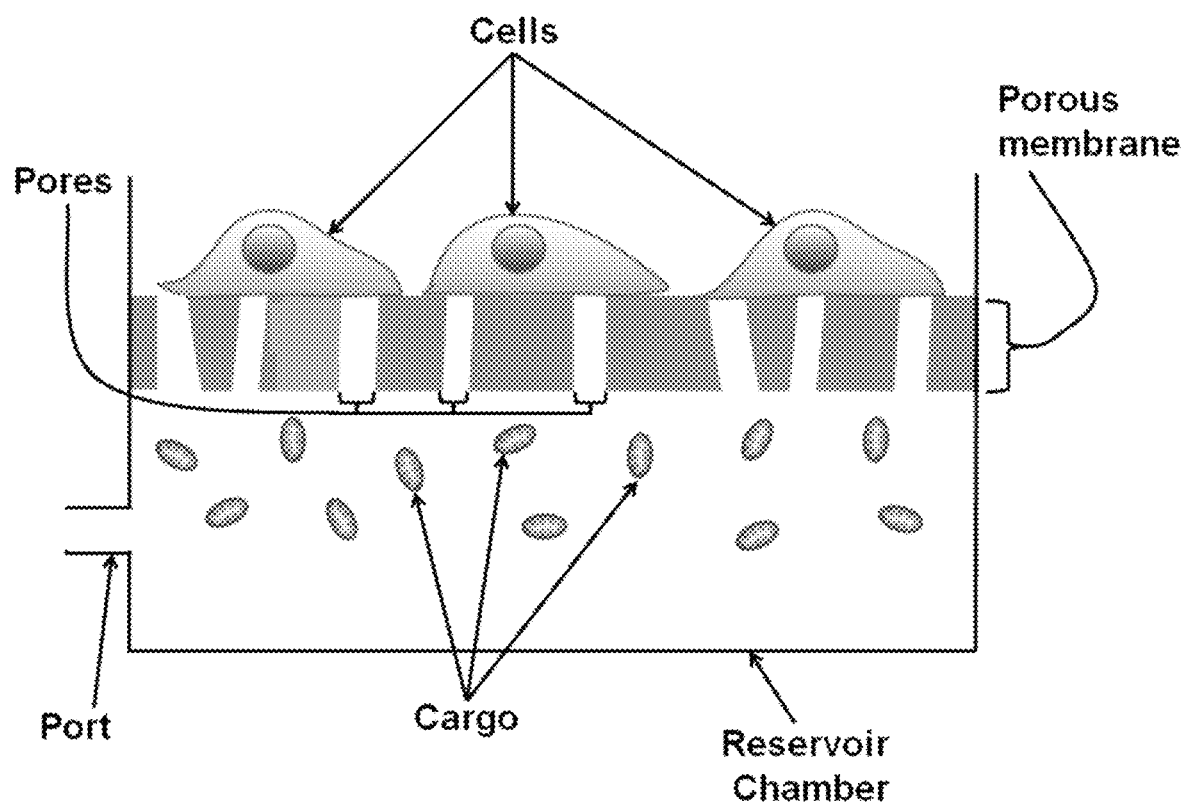
FIGS. 2A and 2B show schematic illustrations of various non-limiting embodiments of a transfection system as described herein.
Figure 2B:
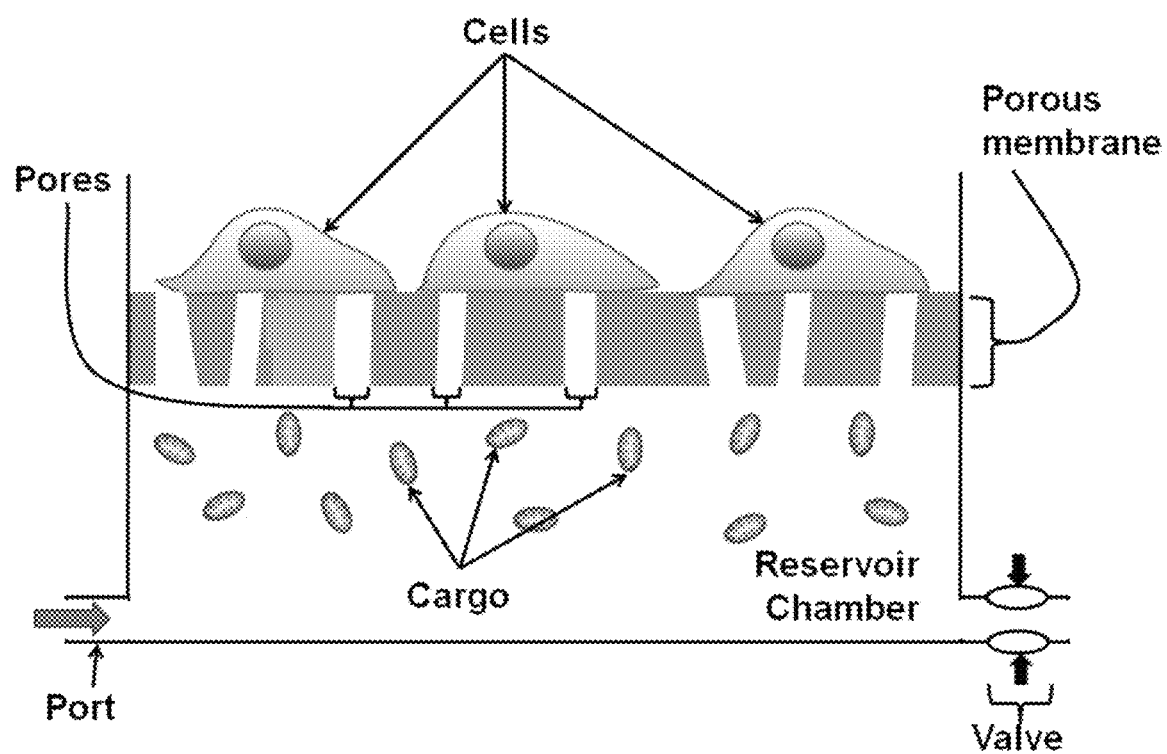

As illustrated in FIG. 2A, the reservoir chamber is configured to contain the cargo that is to be transfected into the recipient cells. The porous membrane is also chosen to support the recipient cells, and in certain embodiments, to permit culturing of those cells as an adherent layer on the porous membrane.

In various embodiments, the cells need not be cultured as an adherent layer. For example, in certain embodiments, the cells are simply adsorbed to the membrane, e.g., by direct deposition and/or by centrifugation. In certain embodiments, the cells are attached to the membrane using various attachment molecules (e.g., integrins, cadherins, selectins, and various synthetic linkers (e.g., heterobifunctional or homobifunctional peptide linkers). In certain embodiments, the cells are "attached" to the membrane by a gel matrix (e.g., gelatin, HYDROMATRIX®, MAXGEL®, collagen gel, hydrogels, and the like).

In certain embodiments the reservoir chamber can be provided with a port and/or channel for introduction of the cargo solution and/or for pressurization of the chamber during a transfection although as explained below, such a port or channel is not required.

In various illustrative, but non-limiting embodiments, the reservoir chamber ranges in volume from about 10 µL, or from about 20 µL, or from about 30 µL, or from about 40 µL, or from about 50 µL, or from about 60 µL, or from about 70 µL, or from about 80 µL up to about 500 µL, or up to about 400 µL, or up to about 300 µL, or up to about 200 µL, or up to about 100 µL.

In various embodiments the porous membrane and/or reservoir chamber are fabricated from essentially any material that is compatible with the eukaryotic cells and cargo that is to be delivered into the cells. Suitable materials include, but are not limited to ceramics, glass, and plastics. In certain embodiments the reservoir chamber is fabricated from a rigid/stiff plastic (e.g., polyethylene, polypropylene, etc.), while in other embodiments, the reservoir chamber is fabricated from a flexible polymer (e.g., PDMS or other polymers).

As indicated above, the transfection methods utilize a porous membrane, and in certain embodiments a flexible porous membrane. Porous membranes are available in a wide variety of materials (e.g., nylon or nylon mesh, filter membranes, polytetrafluoroethylene (PTFE), expanded polytetrafluoroethylene (ePTFE), polyetheretherketone (PEEK), expanded polyetheretherketone (ePEEK), polyethylene (PE), polypropylene (PP), polyvinylidene fluoride (PVDF), ethyl vinyl acetate (EVA), thermoplastic polyurethane (TPU), polyethersulfone (PES), and the like). In certain embodiments, porous rigid materials (e.g., porous ceramic, porous glasses, etc.) are also contemplated. Porous membranes are well known to those of skill in the art and are commercially available in a variety of pore sizes from a number of sources (see, e.g., Porex Corp. Fairburn GA, and the like).

In certain embodiments the porous membrane ranges in thickness from about 3 µm, or from about 5 µm, or from about 7 µm up to about 30 µm, or up to about 25 µm, or up to about 20 µm, or up to about 15 µm, or up to about 10 µm. In certain embodiments the porous membrane is about 10 µm in thickness.

In certain embodiments the average or median pore size of the porous membrane ranges from about 50 nm, or from about 100 nm, or from about 200 nm, or from about 300 nm, or from about 400 nm, or from about 500 nm, or from about 600 nm, or from about 700 nm, or from about 800 nm, or from about 900 nm, or from about 1 µm up to about 30 µm, or up to about 20 µm, or up to about 15 µm, or up to about 10 µm, or up to about 8 µm, or up to about 5 µm. In certain embodiments the median or average pore size in said porous membrane is about 1 µm or about 3 µm, or about 5 µm.

In typical embodiments, the pore density of the membrane is sufficiently high so that on average at least have of the cells thereon are located over at least one pore, or over at least two pores, or over at least 3 pores, or over at least 4 pores, or over at least 5 pores, or over at least 10 pores. In certain embodiments the porous membrane comprises about $1 \times 10^5$ pores/cm$^2$ up to about $1 \times 10^7$ pores/cm$^2$, or about $5 \times 10^5$ pores/cm$^2$ up to about $5 \times 10^6$, or about $1 \times 10^5$ pores/cm$^2$ up to about $1 \times 10^7$ pores/cm$^2$. In certain embodiments the porous membrane comprises about a 1 µm diameter average pore size at about $1.6 \times 10^6$ pores/cm$^2$, or about a 3 µm diameter average pore size at about $8 \times 10^5$ pores/cm$^2$.

There are a number of formats, materials, and size scales that may be used in the construction of the transfection devices described herein and in microfluidic devices that may incorporate them. In some embodiments the transfection devices and, when present, connecting fluid channels and/or ports are comprised of PDMS (or other polymers), and fabricated using soft lithography, while the porous membrane is typically purchased from a vendor of such membranes.

PDMS is an attractive material for fabrication of the devices described herein for a variety of reasons, including but not limited to low cost, optical transparency, ease of molding, and elastomeric character. PDMS also has desirable chemical characteristics, including compatibility with both conventional siloxane chemistries and the requirements of cell culture (e.g. low toxicity, gas permeability). In an illustrative soft lithography method, a master mold is prepared to form one or more reservoir chambers and, when present associated ports and/or channels. This master mold may be produced by a micromachining process, a photolithographic process, or by any number of methods known to those with skill in the art. Such methods include, but are not limited to, wet etching, electron-beam vacuum deposition, photolithography, plasma enhanced chemical vapor deposition, molecular beam epitaxy, reactive ion etching, and/or chemically assisted ion beam milling (Choudhury (1997) *The Handbook of Microlithography, Micromachining, and Microfabrication, Soc. Photo-Optical Instru. Engineer.*; Bard & Faulkner, *Fundamentals of Microfabrication*).

Once prepared the master mold is exposed to a propolymer, which is then cured to form a patterned replica in PDMS. The replica is removed from the master mold, trimmed, and fluid inlets are added where required. The polymer replica may be optionally be treated with a plasma (e.g. an $O_2$ plasma) and bonded to a suitable substrate, such as glass. Treatment of PDMS with $O_2$ plasma generates a surface that seals tightly and irreversibly when brought into conformal contact with a suitable substrate, and has the advantage of generating fluid channel walls that are negatively charged when used in conjunction with aqueous solutions. These fixed charges support electrokinetic pumping that may be used to move fluid through the device. While the above described fabrication of a droplet generating device using PDMS, it should be recognized that numerous other materials can be substituted for or used in conjunction with this polymer. Examples include, but are not limited to, polyolefin plastomers, perfluoropolyethylene, polyurethane, polyimides, and cross-linked phenol/formaldehyde polymer resins.

Transfection Device Operation.

In certain embodiments the methods described herein involve providing "recipient cells" disposed on one side of a porous membrane; providing a cargo in a solution disposed in a reservoir chamber on the opposite side of the porous membrane; and applying pressure to the reservoir chamber sufficient to pass the cargo through pores comprising the porous membrane where the cargo passes through cell membranes and into said cells. In certain embodiments the pressurization of the chamber is accompanied by deformation of the porous membrane.

The cargo-containing solution can be introduced into the reservoir chamber by any of a number of convenient methods. For example, in one illustrative, but non-limiting embodiment, the cargo-containing solution is introduced into the reservoir chamber through a port or channel into that chamber (see, e.g., FIG. 2A).

In another illustrative, but non-limiting embodiment, the reservoir chamber is fabricated as part of a continuous channel. The outflow portion of channel can be configured with a valve. The cargo solution is flowed into and through the chamber. When desired, the valve is closed sealing the reservoir channel and the pressure head can be maintained to provide increased pressure, or the chamber can be further pressurized. The valve is particularly useful when a plurality of reservoir channels are configured along one cargo filling channel (see, e.g., FIG. 7B).

In another illustrative, but non-limiting embodiment, the cargo-containing solution is loaded into the reservoir chamber before placing the porous membrane (e.g., bearing cells) on or in the chamber.

In another illustrative, but non-limiting embodiment, the cargo-containing solution is injected into the reservoir chamber through a needle that penetrates a wall of the reservoir chamber. In such an embodiment, a port or channel for introduction of the cargo solution can readily be eliminated.

In another illustrative, but non-limiting embodiment, the cargo-containing solution can be simply be passed through the porous membrane to load the reservoir chamber.

The reservoir chamber can also be pressurized by any of a number of methods. For example, where the porous chamber is in fluid communication with a channel or port, fluid or gas pressure can be applied to that port using a pump or a gravity feed.

In another illustrative embodiment the reservoir chamber can be sealed and pressure applied by simply deforming inward one or more walls of the reservoir chamber, e.g., manually, using a micromanipulator, pressuring a vessel within which the porous chamber is disposed, using an electromechanical actuator, and the like.

In another illustrative embodiment the reservoir chamber can be sealed and pressure applied by injecting either cargo-containing solution or additional solution into the reservoir channel, e.g., using a syringe, syringe pump, or other injection device.

In certain embodiments the pressure is applied transiently. In various embodiments of such instances the pressure is applied for a period of time ranging from about 1 msec, or from about 10 msec, or from about 20 msec, or from about 50 msec, or from about 80 msec, or from about 100 msec, or from about 500 msec, or from about 1 sec, or from about 5 sec, or from about 10 sec up to about 20 sec, or up to about 30 sec, or up to about 40 sec, or up to about 50 sec, or up to about 1 min, or up to about 1.5 min, or up to about 2 min, or up to about 2.5 min, or up to about 5 min or u to about 10 min. in certain embodiments the pressure is applied for a period of time ranging from about 100 msec up to about 1 min.

The cells are applied to the porous matrix using standard methods. Typically, the cells can be cultured on the porous matrix. This can be done in the transfection device, or alternatively, this can be done separately and the porous matrix bearing cells then transferred to a transfection device. In certain embodiments the cells are cultured as an adherent layer. In certain embodiments the cells are cultured to confluence either before or after the transfection.

The foregoing methods of operation are illustrative and non-limiting. Using the teachings provided herein one of skill can routinely optimize the transfection methods and devices to accommodate particular cell and/or cargo types.

Transfection Systems.

In certain embodiments a plurality of transfection devices are coupled into a transfection system. In such embodiments, each transfection device can be configured to load/transfect a different cargo into the cells present in each device. Thus, for example, in certain embodiments, a single system can provide different loading ports/channels for different transfection devices comprising that system (see, e.g., FIG. 7A). Alternatively, each transfection device comprising the system can be loaded with different cargos using other loading means (e.g., as described herein).

Figure 7A:
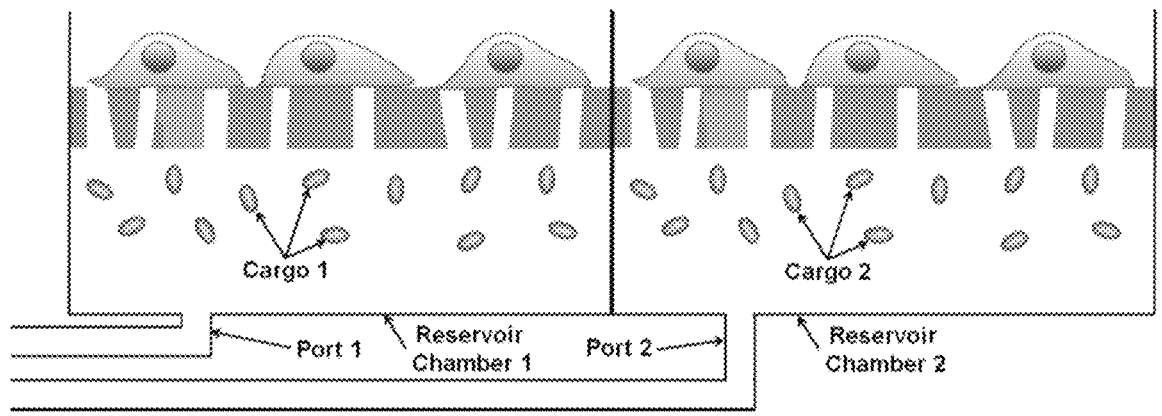
FIGS. 7A and 7B schematically illustrate a plurality of transfection devices integrated into a transfection system. In certain embodiments the transfection devices provide common loading ports/channels for all or for a subset of different transfection devices comprising the system (FIG. 7A) and/or a common cargo loading channel/port (FIG. 7B) for all or for a subset of different transfection devices comprising the system.
Figure 7B:
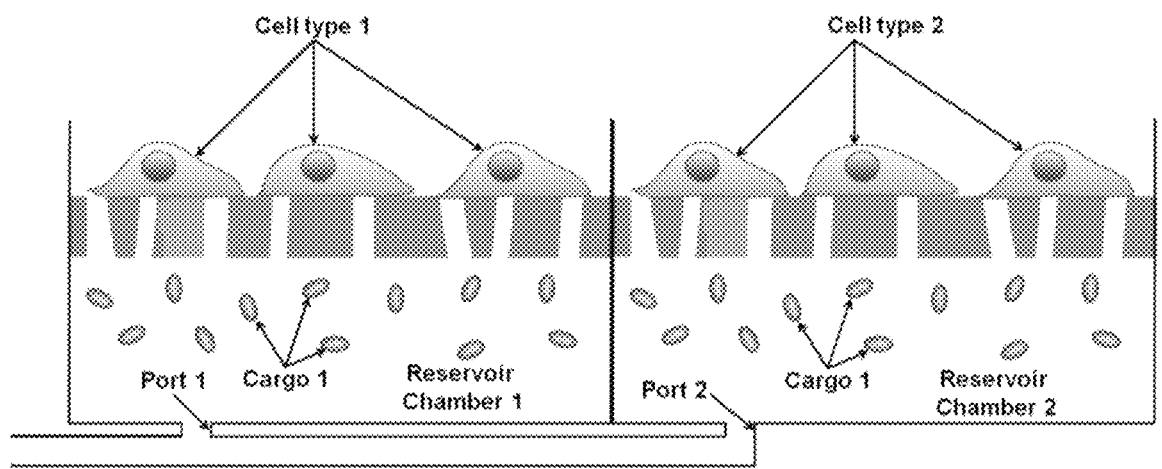

In certain embodiments a single system can provide common loading ports/channels for different transfection devices comprising that system (see, e.g., FIG. 7A). Thus all, or a subset of the transfection devices comprising the system can share a common cargo loading channel/port (see, e.g., FIG. 7B). Different cells can be cultured on the porous membrane comprising each device on a common channel thus facilitating the transfection of different cell types with a common cargo.

In certain embodiments these configurations can be combined in a single system thereby providing subsets of devices that share a common cargo loading channel/port and subsets of devices that have separate cargo loading channels/ports.

It will be appreciated that these configurations are illustrative and non-limiting. Using the teaching provided herein, numerous other configurations will be available to one of skill in the art.

Modular Systems.

In certain embodiments the transfection platforms described herein are provided as a "module" that can readily be integrated with existing equipment. For example, in certain embodiments, the transfect ion substrate is provided in a format that can be added to or that can replace a stage on an existing microscope. In certain embodiments the substrate is formatted to replace and x/y/z stage on an inverted microscope (e.g., a Zeis inverted microscope).

In certain embodiments the transfection substrates are provided as a microfluidic system (e.g., a lab on a chip system) and/or as a module that can be integrated with microfluidic systems.

Deliverable Materials (Cargo).

It is believed possible to deliver essentially any desired material into a cell using the methods and devices described herein. Such materials include, but are not limited to nucleic acids, proteins, organelles, drug delivery particles, probes, labels, and the like. In embodiments, the cargo comprises one or more moieties selected from the group consisting of a natural chromosomes or chromosome fragments, synthetic chromosome, a bacterium, a synthetic particle, an intracellular fungus (e.g., *Pneumocystis jirovecii, Histoplasma capsulatum, Cryptococcus neoformans*, etc.), an intracellular protozoan (e.g., Apicomplexans (e.g., *Plasmodium* spp., *Toxoplasma gondii, Cryptosporidium parvum*), Trypanosomatids (e.g., *Leishmania* spp., *Trypanosoma cruzi*, etc.), and the like), and an organelle (e.g., a nucleus, a nucleolus, a mitochondrion, a chloroplast, a ribosome, a lysosome, and the like).

In certain embodiments the cargo comprises a nucleus, and/or a chloroplast, and/or a nucleolus, and/or a mitochondrion.

In certain embodiments the cargo comprises a whole chromosome, or a chromosome fragment, or a synthetic chromosome (e.g., a BACs (bacterial artificial chromosome)). It is believed the devices and methods described herein can be used to deliver whole or partial natural or synthetic chromosomes. Similar to BACs, large chromosomes or chromosomal fragments that cannot be transduced into most cell types by previous methods can be transferred into cells by the method described herein, for example, inter alia, to establish models of human trisomy disorders (e.g., Down and Klinefelter syndromes).

In certain embodiments the cargo comprises intracellular pathogens, including but not limited to various bacteria, fungi, and protozoans. The transfection of various inanimate particles is also contemplated. Such particle include, but are not limited to quantum dots, surface-enhanced, Raman scattering (SERS) particles, microbeads, and the like.

It will be recognized that these cargos are intended to be illustrative and non-limiting. Using the teachings provided herein, numerous other cargos, especially large cargos, can be transfected into cells.

Cell Types

It is believed the methods and devices described herein can be used with essentially any cell having a cell membrane. Accordingly, in various embodiments, it is contemplated that essentially any eukaryotic cell can be transfected using the methods and devices described herein. Thus, for example, suitable cells that can be transfected using the methods described herein include, but are not limited to vertebrate cells, fungal cells, and yeast cells. In certain embodiments the cells are mammalian cells, insect cells, or invertebrate cells.

Commonly, the methods described herein will be performed with mammalian cells including both human mammalian cells and non-human mammalian cells (e.g., non-human primates, canines, equines, felines, porcines, bovine, ungulates, largomorphs, and the like).

In certain embodiments, the transfected cells comprise stem cells or committed progenitor cells. In certain embodiments the stem cells include adult stem cells, fetal stem cells, cord blood stem cells, acid-reverted stem cells, and induced pluripotent stem cells (IPSCs).

In certain embodiments the cells comprise lymphocytes or other differentiated somatic cells.

In certain embodiments the cells comprise cells from a cell line. Suitable cell lines include for example, HeLa, National Cancer Institute's 60 cancer cell lines (NCI60), ESTDAB database, DU145 (prostate cancer), Lncap (prostate cancer), MCF-7 (breast cancer), MDA-MB-438 (breast cancer), PC3 (prostate cancer), T47D (breast cancer), THP-1 (acute myeloid leukemia), U87 (glioblastoma), SHSY5Y Human neuroblastoma cells, cloned from a myeloma, Saos-2 cells (bone cancer), and the like.

In certain embodiments suitable cell lines include, but are not limited to cell lines listed in Table 1.

In various embodiments the cells are cultured on the porous membrane (e.g., for 1 hour or longer, or for 2 hours or longer or for 4 hours or longer, or for 6 hours or longer or for 12 hours or longer, or for 1 day or longer, or for 2 days or longer, or for 3 days or longer, or for 4 days or longer, or for 5 days or longer, or for 6 days or longer, or for 1 week or longer, or for 2 weeks or longer.

TABLE 1

Illustrative, but non-limiting cells that can be transfected using the methods described herein.

| Cell line | Organism | Origin tissue |
| --- | --- | --- |
| 293-T | Human | Kidney (embryonic) |
| 3T3 cells | Mouse | Embryonic fibroblast |
| 4T1 | murine | breast |
| 721 | Human | Melanoma |
| 9L | Rat | Glioblastoma |
| A2780 | Human | Ovary |
| A2780ADR | Human | Ovary |
| A2780cis | Human | Ovary |
| A172 | Human | Glioblastoma |
| A20 | Murine | B lymphoma |
| A253 | Human | Head and neck carcinoma |
| A431 | Human | Skin epithelium |
| A-549 | Human | Lung carcinoma |
| ALC | Murine | Bone marrow |
| B16 | Murine | Melanoma |
| B35 | Rat | Neuroblastoma |
| BCP-1 cells | Human | PBMC |
| BEAS-2B | Human | Lung |
| bEnd.3 | Mouse | Brain/cerebral cortex |
| BHK-21 | Hamster | Kidney |
| BR 293 | Human | Breast |

TABLE 1-continued

Illustrative, but non-limiting cells that can be transfected using the methods described herein.

| Cell line | Organism | Origin tissue |
|---|---|---|
| BxPC3 | Human | Pancreatic adenocarcinoma |
| C2C12 | Mouse | Myoblast cell line |
| C3H-10T1/2 | Mouse | Embryonic mesenchymal cell line |
| C6/36 | Asian tiger mosquito | Larval tissue |
| C6 | Rat | Glioma |
| Cal-27 | Human | Tongue |
| CGR8 | Mouse | Embryonic Stem Cells |
| CHO | Hamster | Ovary |
| COR-L23 | Human | Lung |
| COR-L23/CPR | Human | Lung |
| COR-L23/5010 | Human | Lung |
| COR-L23/R23 | Human | Lung |
| COS-7 | Monkey | Kidney |
| COV-434 | Human | Ovary |
| CML T1 | Human | CML acute phase |
| CMT | Dog | Mammary gland |
| CT26 | Murine | Colorectal carcinoma |
| D17 | Canine | Osteosarcoma |
| DH82 | Canine | Histiocytosis |
| DU145 | Human | Androgen insensitive carcinoma |
| DuCaP | Human | Metastatic prostate cancer |
| E14Tg2a | Mouse | |
| EL4 | Mouse | |
| EM2 | Human | CML blast crisis |
| EM3 | Human | CML blast crisis |
| EMT6/AR1 | Mouse | Breast |
| EMT6/AR10.0 | Mouse | Breast |
| FM3 | Human | Metastatic lymph node |
| H1299 | Human | Lung |
| H69 | Human | Lung |
| HB54 | Hybridoma | Hybridoma |
| HB55 | Hybridoma | Hybridoma |
| HCA2 | Human | Fibroblast |
| HEK-293 | Human | Kidney (embryonic) |
| HeLa | Human | Cervical cancer |
| Hepa1c1c7 | Mouse | Hepatoma |
| High Five cells | Insect (moth) | Ovary |
| HL-60 | Human | Myeloblast |
| HMEC | Human | |
| HT-29 | Human | Colon epithelium |
| HUVEC | Human | Umbilical vein endothelium |
| Jurkat | Human | T cell leukemia |
| J558L cells | Mouse | Myeloma |
| JY cells | Human | Lymphoblastoid |
| K562 cells | Human | Lymphoblastoid |
| Ku812 | Human | Lymphoblastoid |
| KCL22 | Human | Lymphoblastoid |
| KG1 | Human | Lymphoblastoid |
| KYO1 | Human | Lymphoblastoid |
| LNCap | Human | Prostatic adenocarcinoma |
| Ma-Mel 1, 2, 3 ... 48 | Human | |
| MC-38 | Mouse | |
| MCF-7 | Human | Mammary gland |
| MCF-10A | Human | Mammary gland |
| MDA-MB-231 | Human | Breast |
| MDA-MB-468 | Human | Breast |
| MDA-MB-435 | Human | Breast |
| MDCK II | Dog | Kidney |
| MDCK II | Dog | Kidney |
| MG63 | Human | Bone |
| MOR/0.2R | Human | Lung |
| MONO-MAC 6 | Human | WBC |
| MRC5 | Human (foetal) | Lung |
| MTD-1A | Mouse | |
| MyEnd | Mouse | |
| NCI-H69/CPR | Human | Lung |
| NCI-H69/LX10 | Human | Lung |
| NCI-H69/LX20 | Human | Lung |
| NCI-H69/LX4 | Human | Lung |
| NIH-3T3 | Mouse | Embryo |
| NALM-1 | | Peripheral blood |
| NW-145 | | |
| OPCN/OPCT cell lines | | |
| Peer | Human | T cell leukemia |
| PNT-1A/PNT 2 | | |
| Raji | human | B lymphoma |
| RBL cells | Rat | Leukemia |
| RenCa | Mouse | |
| RIN-5F | Mouse | Pancreas |
| RMA/RMAS | Mouse | |
| S2 | Insect | Late stage (20-24 hours old) embryos |
| Saos-2 cells | Human | |
| Sf21 | Insect (moth) | Ovary |
| Sf9 | Insect (moth) | Ovary |
| SiHa | Human | Cervical cancer |
| SKBR3 | Human | |
| SKOV-3 | Human | |
| T2 | Human | |
| T-47D | Human | Mammary gland |
| T84 | Human | Colorectal carcinoma/ Lung metastasis |
| 293-T | Human | Kidney (embryonic) |
| 3T3 cells | Mouse | Embryonic fibroblast |
| 4T1 | murine | breast |
| 721 | Human | Melanoma |
| 9L | Rat | Glioblastoma |
| A2780 | Human | Ovary |
| A2780ADR | Human | Ovary |
| A2780cis | Human | Ovary |
| A172 | Human | Glioblastoma |
| A20 | Murine | B lymphoma |
| A253 | Human | Head and neck carcinoma |
| A431 | Human | Skin epithelium |
| A-549 | Human | Lung carcinoma |
| ALC | Murine | Bone marrow |
| B16 | Murine | Melanoma |
| B35 | Rat | Neuroblastoma |
| BCP-1 cells | Human | PBMC |
| BEAS-2B | Human | Lung |
| bEnd.3 | Mouse | Brain/cerebral cortex |
| BHK-21 | Hamster | Kidney |
| BR 293 | Human | Breast |
| BxPC3 | Human | Pancreatic adenocarcinoma |
| C2C12 | Mouse | Myoblast cell line |
| C3H-10T1/2 | Mouse | Embryonic mesenchymal cell line |
| C6/36 | Asian tiger mosquito | Larval tissue |
| C6 | Rat | Glioma |
| Cal-27 | Human | Tongue |
| CHO | Hamster | Ovary |
| COR-L23 | Human | Lung |
| COR-L23/CPR | Human | Lung |
| COR-L23/5010 | Human | Lung |
| COR-L23/R23 | Human | Lung |
| COS-7 | Ape | Kidney |
| COV-434 | Human | Ovary |
| CML T1 | Human | CML acute phase |
| CMT | Dog | Mammary gland |
| CT26 | Murine | Colorectal carcinoma |
| D17 | Canine | Osteosarcoma |
| DH82 | Canine | Histiocytosis |
| DU145 | Human | Androgen insensitive carcinoma |
| DuCaP | Human | Metastatic prostate cancer |
| EL4 | Mouse | |
| EM2 | Human | CML blast crisis |
| EM3 | Human | CML blast crisis |
| EMT6/AR1 | Mouse | Breast |
| EMT6/AR10.0 | Mouse | Breast |
| FM3 | Human | Metastatic lymph node |
| H1299 | Human | Lung |
| H69 | Human | Lung |

TABLE 1-continued

Illustrative, but non-limiting cells that can be transfected using the methods described herein.

| Cell line | Organism | Origin tissue |
|---|---|---|
| HB54 | Hybridoma | Hybridoma |
| HB55 | Hybridoma | Hybridoma |
| HCA2 | Human | Fibroblast |
| HEK-293 | Human | Kidney (embryonic) |
| HeLa | Human | Cervical cancer |
| Hepa1c1c7 | Mouse | Hepatoma |
| High Five cells | Insect (moth) | Ovary |
| HL-60 | Human | Myeloblast |
| HMEC | Human | |
| HT-29 | Human | Colon epithelium |
| HUVEC | Human | Umbilical vein endothelium |
| Jurkat | Human | T cell leukemia |
| J558L cells | Mouse | Myeloma |
| JY cells | Human | Lymphoblastoid |
| K562 cells | Human | Lymphoblastoid |
| Ku812 | Human | Lymphoblastoid |
| KCL22 | Human | Lymphoblastoid |
| KG1 | Human | Lymphoblastoid |
| KYO1 | Human | Lymphoblastoid |
| LNCap | Human | Prostatic adenocarcinoma |
| Ma-Mel 1, 2, 3 . . . 48 | Human | |
| MC-38 | Mouse | |
| MCF-7 | Human | Mammary gland |
| MCF-10A | Human | Mammary gland |
| MDA-MB-231 | Human | Breast |
| MDA-MB-468 | Human | Breast |
| MDA-MB-435 | Human | Breast |
| MDCK II | Dog | Kidney |
| MDCK II | Dog | Kidney |
| MG63 | Human | Bone |
| MOR/0.2R | Human | Lung |
| MONO-MAC 6 | Human | WBC |
| MRC5 | Human (foetal) | Lung |
| MTD-1A | Mouse | |
| MyEnd | Mouse | |
| NCI-H69/CPR | Human | Lung |
| NCI-H69/LX10 | Human | Lung |
| NCI-H69/LX20 | Human | Lung |
| NCI-H69/LX4 | Human | Lung |
| NIH-3T3 | Mouse | Embryo |
| NALM-1 | | Peripheral blood |
| NW-145 | | |
| OPCN/OPCT cell lines | | |
| Peer | Human | T cell leukemia |
| PNT-1A/PNT 2 | | |
| PTK2 | Rat Kangaroo | kidney |
| Raji | human | B lymphoma |
| RBL cells | Rat | Leukaemia |
| RenCa | Mouse | |
| RIN-5F | Mouse | Pancreas |
| RMA/RMAS | Mouse | |
| Saos-2 cells | Human | |
| Sf21 | Insect (moth) | Ovary |
| Sf9 | Insect (moth) | Ovary |
| SiHa | Human | Cervical cancer |
| SKBR3 | Human | |
| SKOV-3 | Human | |
| T2 | Human | |
| T-47D | Human | Mammary gland |
| T84 | Human | Colorectal carcinoma/ Lung metastasis |
| THP1 cell line | Human | Monocyte |
| U373 | Human | Glioblastoma-astrocytoma |
| U87 | Human | Glioblastoma-astrocytoma |
| U937 | Human | Leukemic monocytic lymphoma |
| VCaP | Human | Metastatic prostate cancer |
| Vero cells | African green monkey | Kidney epithelium |
| WM39 | Human | Skin |
| WT-49 | Human | Lymphoblastoid |
| X63 | Mouse | Melanoma |
| YAC-1 | Mouse | Lymphoma |
| YAR | Human | B cell |

It will be appreciated that the foregoing cell types are intended to be illustrative and non-limiting. It will be recognized that numerous other eukaryotic cell types can readily be used in the methods and devices described herein. Kits.

EXAMPLES

The following examples are offered to illustrate, but not to limit the claimed invention.

Example 1

Delivery of Large Cargos Into Cells on a Porous Substrate

Figure 3:
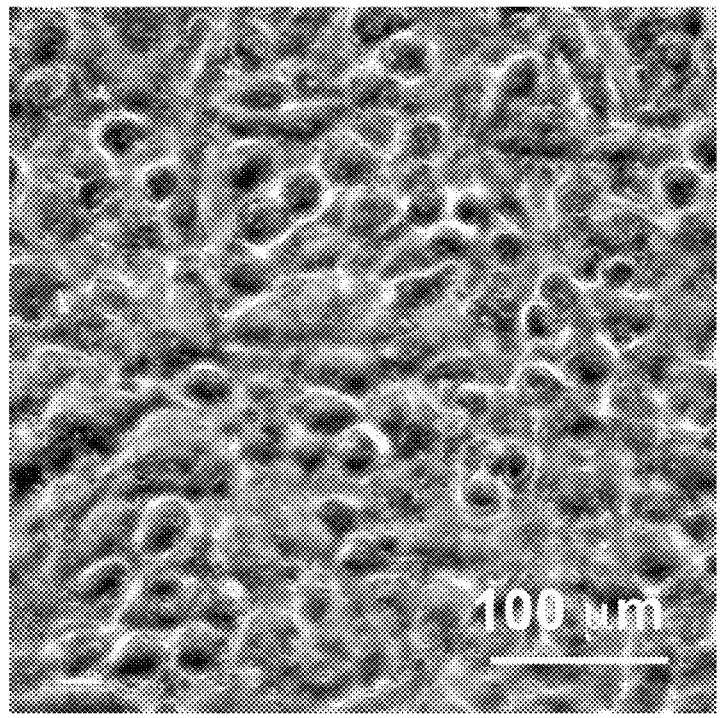
FIG. 3 shows recipient 143BTK rho(0) cells on the porous membrane after mitochondria delivery. Delivered DsRed labeled mitochondria can be observed inside cells and inside membrane pores.

We demonstrated delivery of isolated functional mitochondria into mtDNA depleted rho(0) cells and obtained transformed rho(0) cell lines containing the donor cell mitochondrial genome. The frequency of obtaining a stably transformed transmitochondrial cell line is ~$10^{-4}$, corresponding to dozens of colonies from each delivery experiment-practically, transmitochondrial cell lines will be obtained every time. The delivery process is depicted in FIG. 1. Recipient cells were cultured on a 10 μm thick polymer membrane with through-membrane pores (1 μm diameter pores at $1.6 \times 10^6$ pores/cm$^2$ or 3 μm pores at $8 \times 10^5$ pores/cm$^2$). Mitochondria from donor cells were isolated and the mitochondria suspension (protein concentration 10 mg/mL) was loaded into the reservoir chamber on the opposite side of the polymer membrane. In particular embodiments, the method was tested using polyester, polycarbonate, and polyethylene terephthalate (PET) membranes. The reservoir chamber has a capacity of 100 μL. Transient pressure is applied to the bottom reservoir chamber to pump the mitochondria suspension through the membrane pores towards the recipient cells. The polymer membrane was deformed slightly due to the pressure driven flow and mitochondria and mitochondria aggregates were observed inside the recipient cells and membrane pores after delivery (FIG. 3).

Figures 4, 5:
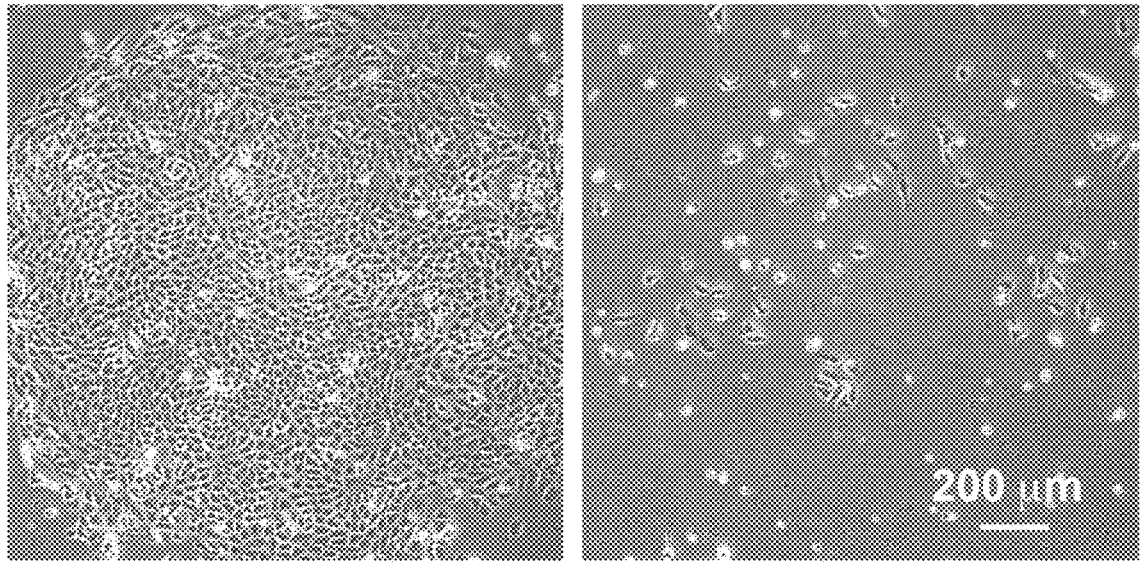
FIG. 4 shows successfully transformed 143BTK rho(0) containing delivered mtDNA formed proliferation centers (left) compared to massive death in rho(0) cells without mtDNA (right) after culturing in restrictive media for 2 weeks.
FIG. 5 shows mitochondria DNA sequence that confirmed that successfully transformed recipient 143BTK rho(0) cells contains mtDNA identical to that of the mitochondria donor cell line MDAMB453 and different from its parental cell line 143BTK. 143BTK (SEQ ID NO:1), 143BTK rho(0) (SEQ ID NO:2), MDAMB453 (SEQ ID NO:3).
Figure 6:
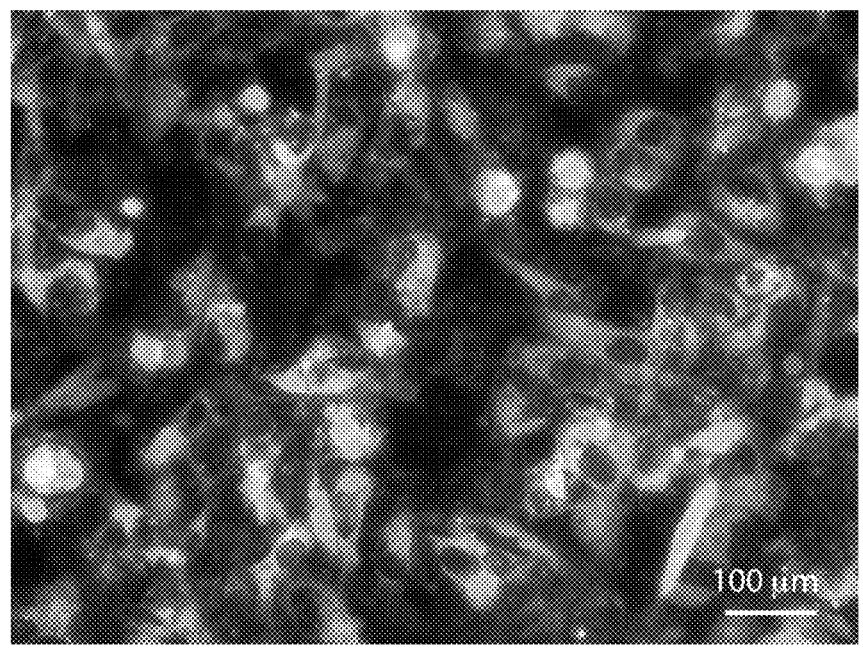
FIG. 6 shows that bacteria delivery efficiency of 84% was obtained using an approach described herein. Nine hours post-delivery, HeLa cells were stained for nucleus (blue) and plasma membrane (red). Delivered GFP bacteria (green) replicated inside the cell cytosol.

Cells were harvested 24 hours after delivery and cultured in restrictive medium to select for successful transformants containing delivered mitochondria (FIG. 4). Direct sequencing of the mitochondria DNA in the D-loop hypervariable region further confirmed that the transformant colonies contained mtDNA that originated from the delivered donor cell mitochondria (FIG. 5).

To compare mitochondria delivery efficiency, the following experiments were also performed:

(A) 100 μL of mitochondria suspension was added to the recipient cells cultured on the porous membrane and co-incubated for 24 hrs; and (B) 100 μL of mitochondria suspension was spun onto the porous membrane followed by seeding the recipient cells and incubate for 24 hrs.

Table 2 lists the number of transformant colonies and transformant frequencies from these experiments. No viable colonies were obtained using method (A) and (B).

TABLE 2

Comparison of mitochondria delivery efficiency.

| Delivery method | Number of transformed colonies | Transformant frequency |
|---|---|---|
| Pumping mitochondria suspension through porous membrane | 49 | $3.3 \times 10^{-4}$ |
| (A) Co-incubation of donor mitochondria with recipient cells | 0 | 0 |
| (B) Seed recipient cells onto donor mitochondria | 0 | 0 |

Using our delivery method, we have generated reproducibly several transmitochondrial cell lines with different mitochondrial genomes. Current results are summarized in Table 3.

TABLE 3

Summary of transmitochondrial lines generated using this delivery method

| Mitochondria donor cell | HEK293 | 143BTK | MDAMB453 | MDAMB453 |
|---|---|---|---|---|
| Recipient cell | 143BTK rho(0) | GFP 143BTK rho(0) | GFP 143BTK rho(0) | 143BTK rho(0) |
| # of delivered cells per trial | $1 \times 10^5$ | $5 \times 10^5$ | $5 \times 10^5$ | $1.5 \times 10^5$ |
| # of transformed colonies | 100 | 10 | 27 | 49 |
| Transformant frequency | $1 \times 10^{-3}$ | $2 \times 10^{-5}$ | $5.4 \times 10^{-5}$ | $3.3 \times 10^{-4}$ |

To demonstrate delivery or bacteria, HeLa cells which are non-phagocytic and do not internalize bacteria efficiently were cultured on the polymer membrane with 3 μm pores. GFP *Francisella novicida* bacteria suspension at $10^{10}$ bacteria/mL was loaded into the reservoir chamber. Following fluid pumping and bacteria delivery, cells were treated with high concentration of antibiotics (10 mg/mL Gentamicin) for 30 minutes to kill extracellular bacteria. After 9 hours of incubation, 84% of HeLa cells contain intracellular bacteria as seen by GFP bacteria replicating inside the cell cytosol (FIG. 6).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of delivering a large cargo into eukaryotic cells, said method comprising:
   providing said cells disposed on one side of a porous polymer membrane that comprises a plurality of pores;
   providing said cargo suspended in a solution disposed in a reservoir chamber on the opposite side of said porous membrane, wherein said cargo ranges in size from the size of a nucleic acid in a lipid or liposomal complex up to the size of an organelle; and
   applying pressure to said reservoir chamber sufficient to pass said cargo through said plurality of pores and through the cell membranes of said cells and into said cells to provide cells transfected with said cargo, wherein said cargo comprises an organelle or a synthetic particle selected from the group consisting of a surface-enhanced Raman scattering (SERS) particle, a quantum dot, and a microbead.

2. The method of claim 1, wherein said cargo comprises a synthetic particle selected from the group consisting of a surface-enhanced Raman scattering (SERS) particle, a quantum dot, and a microbead.

3. The method of claim 1, wherein said cargo comprises an organelle selected from the group consisting of a cell nucleus, a mitochondrion, a nucleolus, a lysosome, and a chloroplast.

4. The method of claim 1, wherein said reservoir chamber ranges in volume from about 10 μL up to about 500 μL.

5. The method of claim 1, wherein said porous membrane ranges in thickness from about 5 μm to about 30 μm.

6. The method of claim 1, wherein:
   the average or median pore size of said porous membrane ranges from about 100 nm up to about 20 μm; and
   the thickness of said porous membrane ranges from about 5 μm to about 20 μm.

7. The method of claim 1, wherein said porous membrane comprises about $1 \times 10^5$ pores/cm$^2$ up to about $1 \times 10^7$ pores/cm$^2$.

8. The method of claim 1, wherein said porous membrane comprises:
   about a 1 μm diameter average pore size at about $1.6 \times 10^6$ pores/cm$^2$; or
   about a 3 μm diameter average pore size at about $8 \times 10^5$ pores/cm$^2$.

9. The method of claim 1, wherein said porous membrane comprises a material selected from the group consisting of a nylon membrane, a nylon mesh, a polytetrafluoroethylene (PTFE) membrane, an expanded polytetrafluoroethylene (ePTFE) membrane, a polyester membrane, a polyetheretherketone (PEEK) membrane, an expanded polyetheretherketone (ePEEK) membrane, aa polyethylene (PE) membrane, a polypropylene (PP) membrane, a polyvinylidene fluoride (PVDF) membrane, an ethyl vinyl acetate (EVA) membrane, a thermoplastic polyurethane (TPU) membrane, a polyethersulfone (PES) membrane, a polycarbonate membrane, and a polyethylene terephthalate (PET) membrane.

10. The method of claim 1, wherein said applying pressure produces a deflection of said porous membrane.

11. The method of claim 10, wherein said deflection ranges from about 20 μm up to about 500 mm.

12. The method of claim 1, wherein:
   said applying pressure comprises applying pressure through a port into said reservoir chamber; or
   said applying pressure comprises deflecting a wall of said reservoir chamber when said chamber is filled and closed; or
   said applying pressure comprises injecting a solution through a wall of said reservoir chamber.

13. The method of claim 1, wherein:
   said providing said cargo suspended in a solution disposed in a reservoir chamber comprises introducing said solution through a port into said reservoir chamber; or
   said providing said cargo suspended in a solution disposed in a reservoir chamber comprises pipetting the cargo solution into the reservoir; or
   said providing said cargo suspended in a solution disposed in a reservoir chamber comprises loading said reservoir chamber before placing said porous membrane on or in said chamber; or
   said providing said cargo suspended in a solution disposed in a reservoir chamber comprises injecting said solution through a needle that penetrates a wall of said reservoir chamber; or
   said providing said cargo suspended in a solution in a reservoir chamber comprises passing said solution through said porous membrane to load said reservoir chamber.

14. The method of claim 1, wherein said cells comprise stem cells selected from the group consisting of adult stem cells, embryonic stem cells, cord blood stem cells and induced pluripotent stem cells.

15. The method of claim 1, wherein said cells are attached to said porous membrane by one or more of the following: adsorption, adhesion molecules, a centrifugal force, and a gel matrix.

16. The method of claim 1, wherein said cells are cultured on said porous membrane.

17. The method of claim 16, wherein said cells are cultured as an adherent layer on said porous membrane.

18. The method of claim 1, wherein said porous membrane does not bear a metallic film or metallic nanoparticles and said method does not involve heating a surface of said porous membrane.

19. The method of claim 1, wherein said cells are selected from the group consisting of mammalian cells, insect cells, and invertebrate cells.

* * * * *